(12) United States Patent
Rahbar et al.

(10) Patent No.: US 9,855,233 B2
(45) Date of Patent: Jan. 2, 2018

(54) METHODS OF QUANTIFYING $N^2$-(1-CARBOXYETHYL)-2'-DEOXY-GUANOSINE (CEDG) AND SYNTHESIS OF OLIGONUCLEOTIDES CONTAINING CEDG

(71) Applicants: CITY OF HOPE, Duarte, CA (US); Mahin Rahbar, Beverly Hills, CA (US)

(72) Inventors: Samuel Rahbar, Beverly Hills, CA (US); Timothy W. Synold, Monrovia, CA (US); John Termini, Altadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/536,299

(22) Filed: Nov. 7, 2014

(65) Prior Publication Data
US 2015/0290156 A1 Oct. 15, 2015

Related U.S. Application Data

(60) Continuation of application No. 13/308,433, filed on Nov. 30, 2011, now abandoned, which is a division of
(Continued)

(51) Int. Cl.
| | |
|---|---|
| *G01N 30/72* | (2006.01) |
| *A61K 31/195* | (2006.01) |
| *G01N 30/04* | (2006.01) |
| *G01N 30/88* | (2006.01) |
| *A61K 45/06* | (2006.01) |
| *A61N 5/10* | (2006.01) |

(52) U.S. Cl.
CPC ....... *A61K 31/195* (2013.01); *G01N 30/7233* (2013.01); *G01N 30/7266* (2013.01); *A61K 45/06* (2013.01); *A61N 5/10* (2013.01); *G01N 2030/045* (2013.01); *G01N 2030/8827* (2013.01); *G01N 2030/8868* (2013.01); *G01N 2800/042* (2013.01)

(58) Field of Classification Search
None
See application file for complete search history.

(56) References Cited

U.S. PATENT DOCUMENTS 6,821,731 B2 11/2004 Gillis et al.

FOREIGN PATENT DOCUMENTS

| WO | WO 93/12258 | 6/1993 |
| WO | WO 2008/145384 A1 | 12/2008 |

OTHER PUBLICATIONS

Agadjanyan, Z.S., et al., "Cumene Peroxide and Fe2+-Ascorbate-induced Lipid Peroxidation and Effect of Phosphoglucose Isomerase," Mol. Cell. Biochem. 289:49-53 (2006).
(Continued)

*Primary Examiner* — Joseph G Dauner
(74) *Attorney, Agent, or Firm* — Perkins Coie LLP; Lara J. Dueppen; Courtney Prochnow

(57) ABSTRACT

Methods of quantifying a $N^2$-carboxyethyl-2'-deoxyguanosine (CEdG) levels in biological samples and comparing those levels to known normal levels can diagnose a number of disorders, including diabetes and cancer. Methods can also determine whether therapies for disorders are effective by measuring CEdG levels before and after treatment. Measurement of CEdG levels occurs using liquid chromatography electrospray ionization tandem mass spectrometry.

3 Claims, 21 Drawing Sheets

Related U.S. Application Data application No. 12/538,854, filed on Aug. 10, 2009, now abandoned.

(60) Provisional application No. 61/087,393, filed on Aug. 8, 2008.

(56) References Cited

OTHER PUBLICATIONS

Ahmed, N., et al., "Methylglyoxal-Derived Hydroimidazolone Advanced Glycation End-Products of Human Lens Proteins," Invest. Ophthalmol. Vis. Sci. 44:5287-5292 (2003).
Ahmed, N., et al., "Quantitative Screening of Protein Biomarkers of Early Glycation, Advanced Glycation, Oxidation and Nitrosation in Cellular and Extracellular Proteins by Tandem Mass Spectrometry Multiple Reaction Monitoring," Biochem. Soc. Trans. 31:1417-1422 (2003).
Avril, N., et al., "Glucose Metabolism of Breast Cancer Assessed by 18F-FDG PET: Histologic and Immunohistochemical Tissue Analysis," J. Nucl. Med. 42:9-16 (2001).
Beisswenger, P., et al., "Metformin Inhibition of Glycation Processes," Diabetes Metab. 29:6S95-6S103 (2003).
Beisswenger, P. J., et al., "Metformin Reduces Systemic Methylglyoxal Levels in Type 2 Diabetes," Diabetes 48:198-202 (1999).
Besaratinia, A., et al., "Similar Mutagenicity of Photoactivated Porphyrins and Ultraviolet a Radiation in Mouse Embryonic Fibroblasts: Involvement of Oxidative DNA Lesions in Mutagenesis," Biochem. 43:15557-15566 (2004).
Bidmon, C., et al., "Analysis of DNA-Bound Advanced Glycation End-Products by LC and Mass Spectrometry," J. Chromatography 855:51-58 (2007).
Bierhaus, A., et al., "Understanding RAGE, The Receptor for Advanced Glycation End Products," J. Mol. Med. 83:876-886 (2005).
Bos, R., et al., "Biologic Correlates of 18Fluorodeoxyglucose Uptake in Human Breast Cancer Measured by Positron Emission Tomography," J. Clin. Oncol. 20:379-387 (2002).
Bourajjaj, M., et al., "Role of Methylglyoxal Adducts in the Development of Vascular Complications in Diabetes Mellitus," Biochem. Soc. Trans. 31:1400-1402 (2003).
Breitling-Utzmann, C. M., et al., "Identification and Quantification of Phosphatidylethanolamine-Derived Glucosylamines and Aminoketones from Human Erythrocytes—Influence of Glycation Products on Lipid Peroxidation," Arch. Biochem. Biophys. 391:245-254 (2001).
Brown, B. E., et al., "Hydrazine Compounds Inhibit Glycation of Low-Density Lipoproteins and Prevent the in Vitro Formation of Model Foam Cells from Glycolaldehyde-Modified Low-Density Lipoproteins," Diabetologia 49:775-783 (2006).
Bulteau, A.L., et al., "Proteasome Inhibition in Glyoxal-treated Fibroblasts and Resistance of Glycated Glucose-6-phosphate Dehydrogenase to 20 S Proteasome Degradation in Vitro," J. Biol. Chem. 276:45662-45668 (2001).
Cadet, J., et al., "Facts and Artifacts in the Measurement of Oxidative Base Damage to DNA," Free Rad. Res. 29:541-550 (1998).
Cao, H., et al., "Stereospecific Synthesis and Characterization of Oligodeoxyribonucleotides Containing an N2-(1-Carboxyethyl)-2'-Deoxyguanosine," J. Am. Chem. Soc. 129:12123-12130 (2007).
Casazza, J. P., et al., "The Metabolism of Acetone in Rat," J. Biol. Chem. 259:231-236 (1984).
Chao, M.R., et al., "Rapid and Sensitive Quantification of Urinary N7-Methylguanine by Isotope-Dilution Liquid Chromatography/Electrospray Ionization Tandem Mass Spectrometry with On-Line Solid-Phase Extraction," Rapid Commun. Mass Spectrom. 19:2427-2432 (2005).
Chaplen, F. W.R., et al., "Detection of Methylglyoxal as a Degradation Product of DNA and Nucleic Acid Components Treated with Strong Acid," Anal. Biochem. 236:262-269 (1996).
Chaplen, F. W.R., et al. "Evidence of High Levels of Methylglyoxal in Cultured Chinese Hamster Ovary Cells," PNAS USA 95:5533-5538 (1998).
Cowey, S., et al., "The Metabolic Syndrome: A High-Risk State for Cancer?" Am. J. Pathol. 169:1505-1522 (2006).
Creighton, D. J., et al., "Brief History of Glyoxalase I and What We Have Learned About Metal Ion-Dependent, Enzyme-Catalyzed Isomerizations," Arch. Biochem. Biophys. 387:1-10 (2001).
Edelman, D., et al., "Utility of Hemoglobin A1c in Predicting Diabetes Risk," J. Gen. Intern. Med. 19:1175-1180 (2004).
Eriksson, U. J., et al., "Teratogenicity of 3-Deoxyglucosone and Diabetic Embryopathy," Diabetes 47:1960-1966 (1998).
Escodd, "Comparison of Different Methods of Measuring 8-Oxoguanine as a Marker of Oxidative DNA Damage," Free Rad. Res. 32:333-341 (2000).
Feinberg, A. P., et al., "Hypomethylation Distinguishes Genes of Some Human Cancers from Their Normal Counterparts," Nature 301:89-92 (1983).
Figarola, J. L., et al., "LR-90 A New Advanced Glycation Endproduct Inhibitor Prevents Progression of Diabetic Nephropathy in Streptozotocin-Diabetic Rats," Diabetologia 46:1140-1152 (2003).
Figarola, J. L., et al., "Renoprotective and Lipid-Lowering Effects of LR Compounds, Novel Advanced Glycation End Product Inhibitors, in Streptozotocin-Induced Diabetic Rats," Ann. N.Y. Acad. Sci. 1043:767-776 (2005).
Fosmark, D. S., et al., "Increased Serum Levels of the Specific Advanced Glycation End Product Methylglyoxal-Derived Hydroimidazolone are Associated with Retinopathy in Patients with Type 2 Diabetes Mellitus," Metab. Clin. Exper. 55:232-236 (2006).
Freire, A. P., et al., "Anti-Glycation Defences in Yeast," Biochem. Soc. Trans. 31:1409-1412 (2003).
Frischmann, M., et al., "Identification of DNA Adducts of Methylglyoxal," Chem. Res. Toxicol. 18:1586-1592 (2005).
Frolov, A., et al., "Fragmentation Behavior of Glycated Peptides Derived from D-Glucose, D-Fructose and D-Ribose in Tandem Mass Spectrometry," J. Mass Spectrom. 41:1459-1469 (2006).
Fu, M.X., et al., "The Advanced Glycation End Product, Nepsilon-(Carboxymethyl)lysine, Is a Product of both Lipid Peroxidation and Glycoxidation Reactions," J. Biol. Chem. 271:9982-9986 (1996).
Fukunaga, M., et al., "Methylglyoxal Induces Apoptosis Through Oxidative Stress-Mediated Activation of p38 Mitogen-Activated Protein Kinase in Rat Schwann Cells," Ann. N.Y. Acad. Sci. 1043:151-157 (2005).
Gaby, A. R., "Adverse Effects of Dietary Fructose," Alt. Med. Rev. 10:294-306 (2005).
Godschalk, R.W.L., et al., "Influences of DNA Isolation and RNA Contamination on Carcinogen-DNA Adduct Analysis by 32P-Postlabeling," Environ. Mol. Mutagen. 32:344-350 (1998).
Gomes, R. A., et al., "Protein Glycation in *Saccharomyces cerevisiae* Argpyrimidine Formation and Methylglyoxal Catabolism," FEBS J. 272:4521-4531 (2005).
Han, Y., et al., "Plasma Methylglyoxal and Glyoxal are Elevated and Related to Early Membrane Alteration in Young, Complication-Free Patients with Type 1 Diabetes," Mol. Cell. Biochem. 305:123-131 (2007).
Huang, J.S., et al., "Role of Receptor for Advanced Glycation End-Product (RAGE) and the JAK/STAT-Signaling Pathway in AGE-Induced Collagen Production in NRK-49F Cells," J. Cell. Biochem. 81:102-113 (2001).
Inagi, R., et al., "Severe Diabetic Nephropathy Model With Early Development of Nodule-Like Lesions Induced by Megsin Overexpression in RAGE/iNOS Transgenic Mice," Diabetes 55:356-366 (2006).
Kavarana, M. J., et al., "Mechanism-Based Competitive Inhibitors of Glyoxalase I: Intracellular Delivery, In Vitro Antitumor Activities, and Stabilities in Human Serum and Mouse Serum," J. Med. Chem. 42:221-228 (1999).
Koc, H., et al., "Applications of Mass Spectrometry for Quantitation of DNA Adducts," J. Chromatogr. 778:323-343 (2002).

(56) References Cited

OTHER PUBLICATIONS

La Vecchia, C., et al., "A Case-Control Study of Diabetes Mellitus and Cancer Risk," Br. J. Cancer 70:950-953 (1994).

Lee, A. T., et al., "A Role for DNA Mutations in Diabetes-Associated Teratogenesis in Transgenic Embryos," Diabetes 44:20-24 (1995).

Lee, E. K., et al., "Inhibition of Aldose Reductase Enhances HeLa Cell Sensitivity to Chemotherapeutic Drugs and Involves Activation of Extracellular Signal-Regulated Kinases," Anti-Cancer Drugs 13:859-868 (2002).

Lerman, J., "Study Design n Clinical Research: Sample Size Estimation and Power Analysis," Can J. Anaesth. 43(2):184-191 (1996).

Li, H., et al., "N2-Carboxyethyl-20-deoxyguanosine, A DNA Glycation Marker, in Kidneys and Aortas of Diabetic and Uremic Patients," Kidney Int. 69:388-392 (2006).

Li, Y., et al., "Nonenzymatic Glycation of Guanosine 50-Triphosphate by Glyceraldehyde: An In Vitro Study of Age Formation," Bioorganic Chemistry 35:417-429 (2007).

Liu, B.F., et al., "Methylglyoxal Induces Apoptosis Through Activation of p38 Mitogen-Activated Protein Kinase in Rat Mesangial Cells," Kidney Int. 63:947-957 (2003).

Lo, T. W.C., et al. "Binding and Modification of Proteins by Methylglyoxal Under Physiological Conditions: A Kinetic and Mechanistic Study with Na-Acetylarginine, NU-Acetylcysteine, and Na-Acetyllysine, and Bovine Serum Albumin," J. Biol. Chem. 269:32299-32305 (1994).

Lo, T. W. C., et al., "The Reaction of Methylglyoxal with Aminoguanidine Under Physiological Conditions and Prevention of Methylglyoxal Binding to Plasma Proreins," Biochem. Pharmacol. 48:1865-1870 (1994).

Markesbery, W. R., "Oxidative Stress Hypothesis in Alzheimer's Disease," Free Radical Biol. Med. 23:134-147 (1997).

Miyata, T., et al., "Glyoxalase I Deficiency is Associated With an Unusual Level of Advanced Glycation End Products in a Hemodialysis Patient," Kidney Int. 60:2351-2359 (2001).

Miyata, T., et al., "Mechanism of the Inhibitory Effect of OPB-9195 [(±)-2-Isopropylidenehydrazono-4-Oxo-Thiazolidin-5-Ylacetanilide] on Advanced Glycation End Product and Advanced Lipoxidation End Product Formation," J. Am. Soc. Nephrol. 11:1719-1725 (2000).

Miyazawa, T., et al., "Tandem Mass Spectrometry Analysis of Amadori-Glycated Phosphatidylethanolamine in Human Plasma," Ann. N.Y. Acad. Sci. 1043:280-283 (2005).

Murata-Kamiya, N., et al., "Methylglyoxal Induces G:C to C:G and G:C to T:A Transversions in the supF Gene on a Shuttle Vector Plasmid Replicated in Mammalian Cells," Mut. Res. 468:173-182 (2000).

Nakagawa, K., et al., "Ion-Trap Tandem Mass Spectrometric Analysis of Amadori-Glycated Phosphatidylethanolamine in Human Plasma With or Without Diabetes," J. Lipid Res. 46:2514-2524 (2005).

Nemet, I., et al., "Methylglyoxal in Food and Living Organisms," Mol. Nutr. Food Res. 50:1105-1117 (2006).

Norberg, M., et al., "A Combination of HbA1c, Fasting Glucose and BMI is Effective in Screening for Individuals at Risk of Future Type 2 Diabetes: OGTT is Not Needed," J. Intern. Med. 260:263-271 (2006).

Oak, J.H., et al., "Amadori-Glycated Phosphatidylethanolamine Induces Angiogenic Differentiations in Cultured Human Umbilical Vein Endothelial Cells," FEBS Letters 555:419-423 (2003).

Ochs, S., et al., "Reaction of 2'-Deoxyguanosine with Glyceraldehyde," Liebigs Ann. Chem. 851-853 (1994).

Papoulis, A., et al., "Identification of N2-(1-Carboxyethyl)Guanine (CEG) as a Guanine Advanced Glycosylation End Product," Biochem. 34:648-655 (1995).

Phillips, S. A., et al., "Modification of the Glyoxalase System in Streptozotocin-Induced Diabetic Rats," Biochem. Pharmacol. 46:805-811 (1993).

Phillips, S. A., et al., "The Formation of Methylglyoxal from Triose Phosphates: Investigation Using a Specific Assay for Methylglyoxal," Eur. J. Biochem. 212:101-105 (1993).

Pischetsrieder, M., et al., "N2-(1-Carboxyethyl)Deoxyguanosine, A Nonenzymatic Glycation Adduct of DNA, Induces Single-Strand Breaks and Increases Mutation Frequencies," Biochem. Biophys. Res. Comm. 264:544-549 (1999).

Price, D. L., et al., "Chelating Activity of Advanced Glycation End-product Inhibitors," J. Biol. Chem. 276: 48967-48972 (2001).

Rachman, H., et al., "Critical Role of Methylglyoxal and AGE in Mycobacteria-Induced Macrophage Apoptosis and Activation," PLoS One 1:e29 (2006).

Rahbar, S., "Novel Inhibitors of Advanced Glycation Endproducts," Arch. Biochem. Biophys. 419:63-79 (2003).

Rahbar, S., "Novel Inhibitors of Glycation and AGE Formation," Cell Biochem. Biophys. 48:147-157 (2007).

Rahbar, S., et al., "Studies of an Unusual Hemoglobin in Patients with Diabetes Mellitus," Biochem. Biophys. Res. Commun. 36:838-843 (1969).

Rahbar, S., "The Discovery of Glycated Hemoglobin a Major Event in the Study of Nonenzymatic Chemistry in Biological Systems," Ann. N.Y. Acad. Sci. 1043: 9-19 (2005).

Ravandi, A., et al., "Isolation and Identification of Glycated Aminophospholipids from Red cells and Plasma of Diabetic Blood," FEBS Letters 381:77-81 (1996).

Rodriguez, H., et al., "Comparison of the Levels of 8-Hydroxyguanine in DNA as Measured by Gas Chromatography Mass Spectrometry Following Hydrolysis of DNA by *Escherichia coli* Fpg Protein or Formic Acid," Nucleic Acids Res. 28:e75 (2000).

Rosenstock, J., et al., "Triple Therapy in Type 2 Diabetes: Insulin Glargine or Rosiglitazone Added to Combination Therapy of Sulfonylurea Plus Metformin in Insulin-Naïve Patients," Diabetes Care 29:554-559 (2006).

Rulli, A., et al., "Expression of Glyoxalase I and II in Normal and Breast Cancer Tissues," Breast Cancer Res. Treat. 66:67-72 (2001).

Sakamoto, H., et al., "Selective Activation of Apoptosis Program by S-p-bromobenzylglutathione Cyclopentyl Diester in Glyoxalase I-Overexpressing Human Lung Cancer Cells," Clin. Cancer Res. 7:2513-2518 (2001).

Schalkwijk, C. G., et al., "Heat-Shock Protein 27 is a Major Methylglyoxal-Modified Protein in Endothelial Cells," FEBS Letters 580:1654-1570 (2006).

Schneider, M., et al., "Detection of DNA-Bound Advanced Glycation End-Products by Immunoaffinity Chromatography Coupled to HPLC-Diode Array Detection," Mol. Nutr. Food Res. 50:424-429 (2006).

Schneider, M., et al., "Determination of Glycated Nucleobases in Human Urine by a New Monoclonal Antibody Specific for N2-Carboxyethyl-2'-Deoxyguanosine," Chem. Res. Toxicol. 17:1385-1390 (2004).

Schupp, N., et al., "Genotoxicity of Advanced Glycation End Products Involvement of Oxidative Stress and of Angiotensin II Type 1 Receptors," Ann. N.Y. Acad. Sci. 1043: 685-695 (2005).

Sebekova, K., et al., "Genomic Damage and Malignancy in End-Stage Renal Failure: Do Advanced Glycation End Products Contribute?" Kidney Blood Press. Res. 30:56-66 (2007).

Seidel, W., et al., "DNA-Glycation Leads to Depurination by the Loss of N2-Carboxyethylguanine In Vitro," Cell. Mol. Biol. 44:1165-1170 (1998).

Seidel, W., et al., "Immunochemical Detection of N2-[1-(1-carboxy)ethyl]guanosine, An Advanced Glycation End Product Formed by the Reaction of DNA and Reducing Sugars or L-Ascorbic Acid In Vitro," Biochim. Biophys. Acta 1425:478-484 (1998).

Shimoi, K., et al., "Oxidative DNA Damage Induced by High Glucose and Its Suppression in Human Umbilical Vein Endothelial Cells," Mut. Res. 480-481:371-378 (2001).

Shinohara, M., et al., "Overexpression of Glyoxalase-I in Bovine Endothelial Cells Inhibits Intracellular Advanced Glycation Endproduct Formation and Prevents Hyperglycemia-Induced Increases in Macromolecular Endocytosis," J. Clin. Invest. 101:1142-1147 (1998).

(56) References Cited

OTHER PUBLICATIONS

Shoda, H., et al., "Inhibitory Effects of Tenilsetam on the Maillard Reaction," Endocrinology 138:1886-1892 (1997).

Singh, R., et al., "Liquid Chromatography-Electrospray Ionization-Mass Spectrometry: The Future of DNA Adduct Detection," Carcinogenesis 27:178-196 (2006).

Suji, G., et al., "DNA Damage by Free Radical Production by Aminoguanidine," Ann. N.Y. Acad. Sci. 1067:191-199 (2006).

Synold, T., et al., "Advanced Glycation End Products of DNA: Quantification of N2-(1-Carboxyethyl)-2'-Deoxyguanosine in Biological Samples by Liquid Chromatography Electrospray Ionization Tandem Mass Spectrometry," Chem. Res. Toxicol. 21:2148-2155 (2008).

Taghizadeh, K., et al., "Quantification of DNA Damage Products Resulting from Deamination, Oxidation and Reaction with Products of Lipid Peroxidation by Liquid Chromatography Isotope Dilution Tandem Mass Spectrometry," Nature Protocols 3:1287-1298 (2008).

Thisted, R. A., "What is a P-Value?" The Univ. of Chicago (1998) http://www.stat.uchicago.edu/~thisted.

Thornalley, P. J., et al., "Advances in Glyoxalase Research. Glyoxalase Expression in Malignancy, Anti-Proliferative Effects of Methylglyoxal, Glyoxalase I Inhibitor Diesters and S-D-Lactoylglutathione, and Methylglyoxal-Modified Protein Binding and Endocytosis by the Advanced Glycation Endproduct Receptor," Crit. Rev. Oncol. Hematol. 20:99-128 (1995).

Thornalley, P. J., et al., "The Enzymatic Defence Against Glycation in Health, Disease and Therapeutics," Biochem. Soc. Trans. 31:1341-1342 (2003).

Thornalley, P. J., et al., "Formation of Glyoxal, Methylglyoxal and 3-Deoxyglucosone in the Glycation of Proteins by Glucose," Biochem. J. 344:109-116 (1999).

Thornalley, P. J., et al., "Glutathione-Dependent Detoxification of α-Oxoaldehydes by the Glyoxalase System: Involvement in Disease Mechanisms and Antiproliferative Activity of Glyoxalase I Inhibitors," Chemico-Biological Interactions 111-112:137-151 (1998).

Thornalley, P. J., et al., "Kinetics and Mechanism of the Reaction of Aminoguanidine with the α-Oxoaldehydes Glyoxal, Methylglyoxal, and 3-Deoxyglucosone Under Physiological Conditions," Biochem. Pharmacol. 60:55-65 (2000).

Thornalley, P. J., "Protecting the Genome: Defence Against Nucleotide Glycation and Emerging Role of Glyoxalase I Overexpression in Multidrug Resistance in Cancer Chemotherapy," Biochem. Soc. Trans. 31:1372-1377 (2003).

Thornalley, P. J., et al., "Quantitative Screening of Advanced Glycation Endproducts in Cellular and Extracellular Proteins by Tandem Mass Spectrometry," Biochem. J. 375:581-592 (2003).

Vaca, C. E., et al., "Formation of DNA Adducts in Human Buccal Epithelial Cells Exposed to Acetaldehyde and Methylglyoxal In Vitro," Chemico-Biological Interactions 108:197-208 (1998).

Van Heijst, J. W., et al., "Advanced Glycation End Products in Human Cancer Tissues: Detection of Nepsilon-(Carboxymethyl)lysine and Argpyrimidine," Ann. N.Y. Acad. Sci. 1043:725-733 (2005).

Van Heijst, J. W.J., et al., "Argpyrimidine-Modified Heat Shock Protein 27 in Human Non-Small Cell Lung Cancer: A Possible Mechanism for Evasion of Apoptosis," Cancer Letters 241:309-319 (2006).

Vander Jagt, D. L., "Methylglyoxal, Diabetes Mellitus and Diabetic Complications," Drug Metab. Drug Interact. 23:93-124(2008).

Vander Jagt, D. L., et al., "Methylglyoxal Metabolism and Diabetic Complications: Roles of Aldose Reductase, Glyoxalase-I, Betaine Aldehyde Dehydrogenase and 2-Oxoaldehyde Dehydrogenase," Chemico-Biological Interactions 143-144:341-351 (2003).

Vander Jagt, D. L., et al., "Reduction of Trioses by NADPH-Dependent Aldo-Keto Reductases," J. Biol. Chem. 267:4364-4369 (1992).

Wautier, J.L., "Protein Glycation: A Firm Link to Endothelial Cell Dysfunction," Circ. Res. 95:233-238 (2004).

Wells-Knecht, K. J., et al., "Mechanism of Autoxidative Glycosylation: Identification of Glyoxal and Arabinose as Intermediates in the Autoxidative Modification of Proteins by Glucose," Biochem. 34:3702-3709 (1995).

Wondrak, G. T., et al., "Identification of α-Dicarbonyl Scavengers for Cellular Protection Against Carbonyl Stress," Biochem. Pharmacol. 63:361-373 (2002).

Wu, L., et al., "Troglitazone Selectively Inhibits Glyoxalase I Gene Expression," Diabetologia 44:2004-2012 (2001).

Yabe-Nishimura, C., et al., "Up-Regulation of Aldose Reductase by the Substrate, Methylglyoxal," Chemico-Biological Interactions 143-144:317-323 (2003).

Yao, D., et al., "Methylglyoxal Modification of mSin3A Links Glycolysis to Angiopoietin-2 Transcription," Cell 124:275-286 (2006).

Yeh, C.H., et al., "Requirement for p38 and p44/p42 Mitogen-Activated Protein Kinases in RAGE-Mediated Nuclear Factor-kB Transcriptional Activation and Cytokine Secretion," Diabetes 50:1495-1504 (2001).

Yim, H.S., et al., "Free Radicals Generated During the Glycation Reaction of Amino Acids by Methylglyoxal," J. Biol. Chem. 270:28228-28233 (1995).

A

B

C

A

B

C

US 9,855,233 B2

METHODS OF QUANTIFYING N²-(1-CARBOXYETHYL)-2'-DEOXY-GUANOSINE (CEDG) AND SYNTHESIS OF OLIGONUCLEOTIDES CONTAINING CEDG

PRIORITY CLAIM

This application is a continuation of U.S. application Ser. No. 13/308,433, filed Nov. 30, 2011, which is a divisional of U.S. application Ser. No. 12/538,854, filed Aug. 10, 2009, which claims the benefit of U.S. Provisional Application Ser. No. 61/087,393, filed Aug. 8, 2008, both of which are incorporated herein by reference.

GOVERNMENT INTEREST

The present invention was made with government support under City of Hope's Cancer Center Support Grant (NIH Grant No. P30 CA33572) and the California Breast Cancer Research Program for a pre-doctoral fellowship to D. Tamae (14GB-0162). The government has certain rights in the present invention.

BACKGROUND

Methylglyoxal (MG) is a highly reactive electrophile and is present at micromolar levels in many foods and most living organisms. MG is a major environmental breakdown product of carbohydrates. MG is also generated biochemically during glycolysis via elimination of phosphate from the common enediol intermediate resulting from deprotonation of dihydroxyacetone phosphate and glyceraldehyde 3-phosphate. Additional endogenous sources of MG include the catabolism of threonine and the P450 mediated oxidation of ketone bodies and the oxidative breakdown of DNA and RNA under acidic conditions. MG is a probable mutagen in vivo.

Methylglyoxal induces G>T and G>C transversions, as well as a large number (50%) of multibase deletions. Since 89% of the base substitution mutations are observed at guanosine, and N²-(1-Carboxyethyl)-2'-Deoxy-Guanosine ("CEdG") is the predominant adduct formed from reaction of MG with DNA, this pattern of transversions arises from CEdG (as primer extension assays using oligonucleotide templates containing CEdG have evidenced). The presence of CEdG in DNA has also been shown to induce single-strand breaks, suggesting an alternative mechanism by which this adduct may contribute to genetic instability.

Glycation results when a sugar, such as fructose or glucose, non-enzymatically links to a protein or lipid. Glycation typically impairs the function of the molecules to which it binds. Methylglyoxal reacts readily with nucleophilic moieties on proteins, lipids and DNA to produce covalent adducts known as advanced glycation end-products (AGEs). Protein AGEs are well characterized and these highly modified proteins have been proposed to play a role in the various pathologies associated with diabetes, cancer, aging, and Alzheimers disease. The first clear correlation between abnormal levels of a protein-AGE and a human disease (diabetes) was described in 1969 for the hemoglobin $HbA_{1c}$ adduct by Rahbar et al. Since then, hemoglobin $HbA_{1c}$ has become a commonly used biomarker for the diagnosis and treatment monitoring of diabetes.[11-13] Accordingly, there is continued interest in the development of novel, more sensitive assays for the quantitative measurement of biomolecule-derived AGEs to complement and extend the clinical biomarker repertoire, as well as to assist in elucidating their role in pathology.

Approximately a dozen protein-AGEs have been characterized and LC-MS/MS methods have been described for their quantitative measurement. Choosing an appropriate protein-AGE biomarker for evaluating the glycation status of a particular target tissue or organ is complicated by unequal protein-AGE distributions across different tissues, varying adduct stabilities, and the limited availability of stable isotope standards for quantification. Glycation adducts of DNA have potential as biomarkers since all nucleated cells contain the same DNA content and should reflect the relative level of MG in the target tissue.

In spite of longstanding interest in the role of biopolymer glycation in human disease, no generally applicable method for the quantitative determination of CEdG has been described. A $^{32}P$ post-labeling assay has been used to estimate endogenous levels of CEdG in human buccal epithelial cells of $2-3/10^7$ nucleotides.[28] However, although the post-labeling method offers potential advantages in sensitivity, a major drawback is that direct analyte verification is not possible. Moreover, post-labeling is prone to artifacts and false positives, and may lead to inaccurate estimation of adduct levels due to several factors including RNA contamination.

An immunoaffinity-based method for the detection of CEdG using a polyclonal antibody coupled to a diode array HPLC platform has more recently been described by Schneider et al in 2006. This approach was used to provide the first demonstration of CEdG in human urine and cultured smooth muscle cells. In some cases, peak identity was confirmed by LC-MS/MS, but quantitation was not practical due to the imprecise nature of immunoaffinity chromatography. A monoclonal-based immunohistochemical detection method has also been reported and was used to demonstrate elevated levels of CEdG in aorta and kidney of diabetic patients relative to normal controls.[31] However, antibody-based assays are primarily of value in qualitative and comparative determinations of adduct abundance.

To date, there are no reliable quantitative methods for CEdG measurement, which is likely due to a lack of suitable isotopically enriched standards and other barriers to a reliable quantitative method. Such a method would be a substantial improvement in the art.

SUMMARY

In a first embodiment, advanced glycation end products (AGE), such as N²-carboxyethyl-2'-deoxyguanosine (CEdG), may be quantified in a biological sample using liquid chromatography electrospray ionization tandem mass spectrometry (LC-ESI-MS/MS) for diagnosis, monitoring, and treatment of pathologies involving metabolic disorders, including abnormal glucose metabolism. Such pathologies include diabetes and cancer, amongst other metabolic diseases or disorders. Quantification is achieved by a stable isotope dilution method using an internal standard. When the AGE is CEdG, the internal standard is $^{15}N_5$-CEdG. The advantage of having two stereoisomers of CEdG that can be resolved and quantitated allows for two independent measurements for the same condition, significantly enhancing the accuracy of the method.

Detecting physiologically elevated or depressed levels of AGE in a sample may indicate that the subject from which the sample was taken has a disease or disorder caused or indicated by such AGE levels. The quantification method allows for a precise determination of AGE amounts and thus, allows for sensitive determination of AGE levels compared to other samples from the same subject at the same time, other samples from the same subject at different time points, or other samples from other subjects, such as a person known not to be affected by a disease. For example, detecting elevated levels of CEdG in a person indicates predisposition to or the presence of hyperglycemia or diabetes. Reaction of double stranded DNA with MG or glucose in vitro produces primarily $N^2$-carboxyethyl-2'-deoxyguanosine as a diastereomeric mixture (FIG. 1). The same type of sample may be used to compare between various AGE levels, such as a comparison between AGE levels in a first tissue sample and a second tissue sample. Alternatively, the AGE levels may be compared between various types of samples so long as the relative physiological normal level for each type of sample is known.

In another embodiment, internal standards for other AGEs are created using the methods disclosed herein for synthesizing the internal standard of CEdG. Standards for MS are typically identical in structure to the intended analyte, but contain stable isotopes (15N, 13C, 18O) in order to give a different mass to an otherwise chemically identical substance. The isotope behaves identically to the intended analyte, has the same retention on chromatography, and undergoes the same chemistry, and is only distinguishable by mass.

In a different embodiment, the quantification methods described herein may also be used to determine the effectiveness of a therapy, which may be a test compound or other protocol, intended to treat or ameliorate an AGE-related disease or disorder (a "therapeutically effective amount"). Before the therapy is administered, a first biological sample is taken. After the therapy has been administered, a second biological sample is taken. Additional biological samples may also be taken at other time points during and/or after the therapy. AGE is quantified in the samples and the difference between AGE levels in the samples is measured. Other known statistical analysis, such as tests for statistical significance, may also be applied. If a successful therapy results in a reduction of the level of AGE and such reduction is noted after the administration of the therapy, it indicates that the therapy may be working for its intended purpose. If AGE levels in the sample are static or increased during the course of the therapy, it indicates that the therapy may not be working for its intended purpose of reducing AGE levels. If a successful therapy results in an increase of AGE levels with a treatment, the opposite analysis would apply: increases in AGE levels would indicate the therapy may be working, whereas static or decreased levels would indicate that the therapy may not be effective.

Kits for quantifying AGE levels, such as CEdG levels, are also contemplated. Such kits facilitate the methods described herein may contain any of the following: standards such as $^{15}N_5$-CEdG, tubes, labels, reagents such as buffer, and instructions for use.

Another embodiment involves measuring urine samples in an animal model to monitor the dose dependency of LR-90 as it decreases CEdG levels in vivo.

Yet another embodiment is measuring the effect of aromatase inhibitors on CEdG levels, and relatedly, on glycation status. CEdG levels are measured in a subject undergoing aromatase inhibitory therapy (AI) to determine the impact of AI on cognitive function and mental acuity.

A method of measuring CEdG to predict chemosensitivity of tumors and to identify cancers that may be treated from targeting glyoxalase 1 and/or aldose reductase to restore chemosensitivity is also described. Tumors with elevated levels of CEdG are more sensitive to chemotherapy. Related methods of inducing production of CEdG or other AGE products in tumor cells or of administering CEdG to tumor cells to induce apoptosis and/or increased sensitivity to chemotherapy are also provided. The effectiveness of radiotherapy may also be tested by measuring CEdG in tumors.

A novel synthesis of oligonucleotides containing site-specifically modified CEdG residues is shown in FIG. 16. Such synthesis facilitates experiments using CEdG, such as experiments that investigate the biological consequences of CEdG substitution in DNA and for serving as internal standards for assays measuring CEdG.

These and other embodiments are further explained by reference to the detailed description.

BRIEF DESCRIPTION OF THE DRAWINGS

FIG. 8A: UV spectra of CEdG(A) (solid line) and CEdG(B) (dotted line) with no isotopic labeling. Both samples were diluted 1:50; $OD_{255}(dG)=12,300$ OD/M. For CEdG(A), XX-49-A, 28.55 mL; diluted $OD_{255}=0.450$; undiluted $OD_{255}=22.50$; conc.=1.83 mM, 52.22 umol @ FW 338.30=17.67 mg. For CEdG(B), XX-49-A, 40.61 mL; diluted $OD_{255}=0.327$; undiluted $OD_{255}=16.35$; conc.=1.33 mM, 53.98 umol @ FW 338.30=18.26 mg. FIG. 8B: $^{15}N_5$-CEdG(A); 2 uL stock diluted to 500; $OD_{255}=1.207$. FIG. 8C: $^{15}N_5$-CEdG(B); 1 uL stock diluted to 500; $OD_{255}=0.883$.

DETAILED DESCRIPTION

Figure 1:
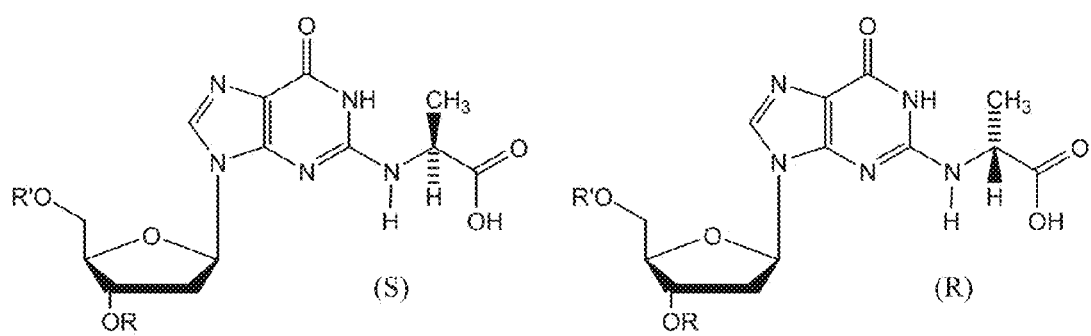
FIG. 1. The two CEdG diastereomers formed from reaction of MG with dG.

Quantitative measurement of advanced glycation end products (AGE) is accomplished using mass spectrometry, such as liquid chromatography electrospray ionization tandem mass spectrometry (LC-ESI-MS/MS) and internal standards designed for each targeted AGE. Such measurements allow for precise determinations of AGE levels, including small or incremental changes in such levels.

Diabetes, metabolic disorders, cancer and other diseases may be diagnosed by measuring $N^2$-carboxyethyl-2'-deoxyguanosine (CEdG) levels alone or in conjunction with other AGE levels in biological samples. CEdG levels are measured using liquid chromatography electrospray ionization tandem mass spectrometry or other reliable means. The CEdG levels from the sample are then compared to physiologically normal CEdG levels. Methods for further determining the efficacy of therapies or treatments applied to those disorders comprise measuring the effect the putative therapeutic have on the CEdG levels in an individual receiving it. The subject having its AGE levels and/or the efficacy of treatment measured is preferably a mammal, such as a human.

Thus, one method of quantifying one or more advanced glycation end products in a sample, comprises obtaining a biological sample from a subject; and performing liquid chromatography electrospray ionizing tandem mass spectrometry assay on the sample using a stable isotope dilution and an internal standard to determine how much AGE is in the sample. When the AGE is $N^2$-carboxyethyl-2'-deoxyguanosine (CEdG), the internal standard is $^{15}$N$_5$-CEdG. With CEdG quantities in hand, abnormal levels may indicate metabolic disorders, cancers, or diabetes. Upon detecting the levels, efficacies of various treatments may be determined using AGE levels as a marker for the success of the treatment.

Metabolic diseases cover a wide range of disorders including carbohydrate metabolism, amino acid metabolism, organic acid metabolism, mitochondrial metabolism, porphyrin metabolism, fatty acid oxidation disorders, purine and pyrimidine metabolism, steroid metabolism, mitochondrial metabolism, peroxisomal and lysosomal storage disorders, and glycolytic metabolic disorders, such as glyolytic cancers. A glycolytic cancer is a cancer that is caused or influenced by abnormal sugar processing, such as with glycation. Conditions which result in the impairment of glucose regulation such as diabetes and metabolic syndrome have been shown to significantly increase the risk for cancers of the breast, liver, pancreas, colon, cervix and endometrium. In the case of hyperglycemia and/or diabetes, an elevated level of CEdG, as compared to normal physiological levels of CEdG, indicates that the subject has diabetes.

A sensitive LC-ESI-MS/MS method for the measurement of CEdG in urine or double-stranded DNA is used. Quantification is achieved by the stable isotope dilution method using synthetic $^{15}$N$_5$-CEdG as an internal standard. Urinary CEdG was measured in normal and streptozoticin-induced diabetic rats, and it was shown that adduct levels are significantly increased following the onset of hyperglycemia. LC-ESI-MS/MS was used to demonstrate a dose-dependent reduction in CEdG in response to administration of LR-90, an inhibitor of AGE formation. Measurement of CEdG from hydrolyzed and dephosphorylated double-stranded DNA was complicated by the fact that MG was present during the enzymatic workup. This was found to react with DNA during sample workup leading to artifactual overestimation of CEdG levels. In order to circumvent this problem, adventitious MG was sequestered by the addition of carbonyl scavengers such as aminoguanidine (AG) and D-penicillamine (D-P) prior to workup, resulting in stable and reproducible determinations. In the case of glycolytic cancers, such as breast cancer, a reduced level of CEdG, as compared to normal physiological levels of CEdG, indicates that the subject has cancer.

Materials and Instrumentation.

$^{15}$N$_5$-2'-deoxyguanosine was purchased from Silantes (Munich, Germany, lot # dG-N-0507-1/2); DL-glyceraldehyde (95%), calf thymus DNA was from Sigma (St. Louis, Mo.), and ammonium acetate (1M, pH 7 solution) from Fluka (Buchs, Switzerland). Phosphate salts were A.C.S. reagent grade from J. T. Baker (Phillipsburg, N.J.). High performance liquid chromatography (HPLC) grade $CH_3CN$ was purchased from Fisher Scientific (Fair Lawn, N.J.). All water was purified to a resistivity of 18.2 MΩ using a Nanopure Diamond system by Barnstead International (Dubuque, Iowa). Solid phase extractions were performed using 1 ml strata-X-C cation mixed mode cartridges (Phenomenex, Torrance Calif.). Nuclease P1 was purchased from US Biologicals (Swampscott, Mass.). Phosphodiesterase II from bovine spleen and alkaline phosphatase from bovine intestinal mucosa was purchased from Sigma-Aldrich. HPLC separations were performed using a Hewlett-Packard Series 1100 Liquid Chromatography system equipped with a diode-array detector. Ultraviolet spectra were collected on an Ultrospec 3000 pro (Amersham Biosciences, Piscataway, N.J.). Mass analysis of synthetic $^{15}N_5$-CEdG was performed using a Thermo Finnigan LTQ-FT linear ion trap mass spectrometer (San Jose, Calif.) in the Mass Spectrometry-Proteomics Core Facility of the City of Hope.

LC-MS/MS analyses of CEdG in biological samples were carried out using a Micromass Quattro Ultima Triple Quadrupole Mass Spectrometer (Beverly, Mass.) interfaced to an Agilent 1100 Capillary HPLC system (Palo Alto, Calif.) equipped with a Synergi $C_{18}$ analytical column (4μ, 150×2.0 mm; Phenomenex, Torrance, Calif.). $^1$H NMR spectra were recorded at 400 MHz on a VNMRS spectrometer (Varian, Inc., Palo Alto, Calif.) in the Synthesis and Biopolymer Core Facility of the City of Hope. 1D and 2D NMR data was processed using the Spinworks shareware program (version 2.5.5), copyright 1999-2006 by Kirk Marat and available from the University of Manitoba website.

Synthesis and Characterization of $^{15}N_5$-CEdG.

Figure 2:
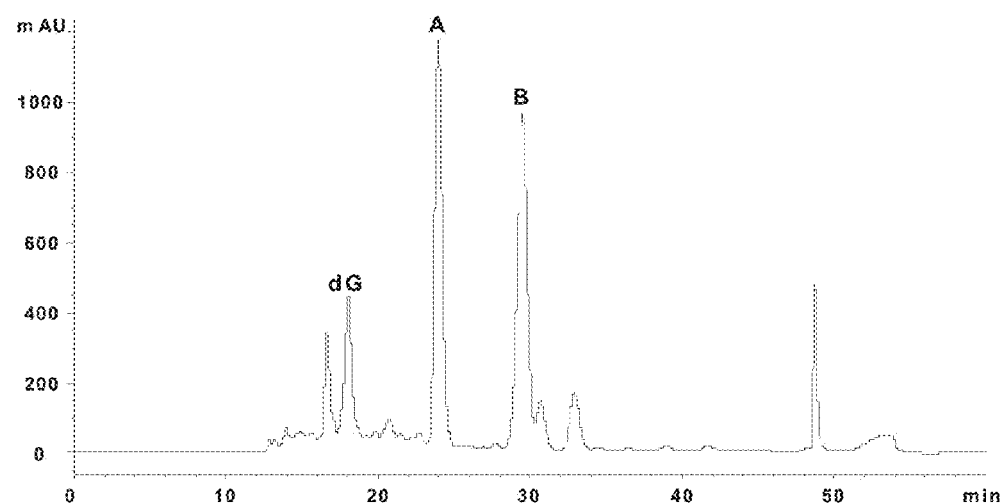
FIG. 2. A representative HPLC chromatogram of the reaction of $^{15}N_5$-dG with dl-glyceraldehyde. Peaks A and B correspond to the two diastereomers of $^{15}N_5$-CEdG.

DL-Glyceraldehyde was used to generate methylgloxal (MG) in situ via guanine catalyzed dehydration.[17] DL-Glyceraldehyde (9.5 mg) was added to 10 mg of $^{15}N_5$-labeled dG, 12.3 mg potassium dihydrogen phosphate, and 24.0 mg disodium hydrogen phosphate in 87.7 μL $H_2O$. The heterogeneous reaction mixture was vortexed and placed in a heat block at 40° C. Reactions were worked up following complete dissolution of solids (~14-17 days) yielding a yellow-red viscous solution. Products were purified by HPLC in 10-15 μL aliquots on a 10×50 mm Waters XTerra MS $C_{18}$ 2.5μ column using a $(Et)_3NH_4OAc$ (50 mM, pH 7)/$CH_3CN$ gradient. The $CH_3CN$ concentration was raised from 0 to 4.0% in the first 5 minutes, from 4.0 to 6.5% over 30 minutes; held at 6.5% for 5 minutes, then raised to 90% to wash residual material off the column. Diastereomers CEdG-A and B eluted at 24 and 29 minutes, respectively (FIG. 2).

Figure 3:
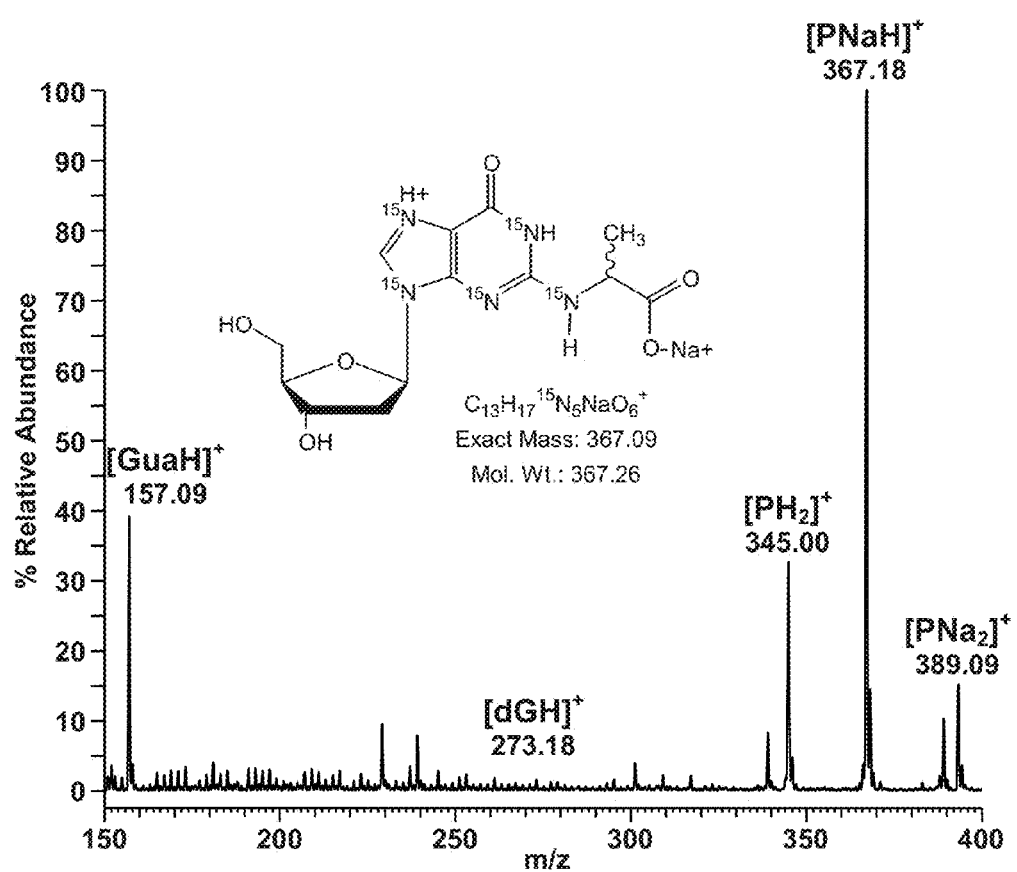
FIG. 3. Full scan positive ion ESI-MS spectrum for $^{15}N_5$-CEdG diastereomer peak A.
Figure 8:
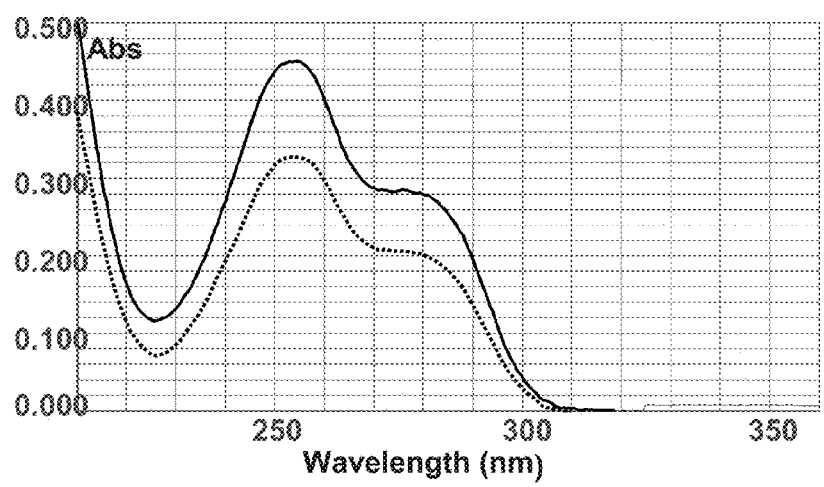
FIG. 8. UV spectra of stock solutions of unlabeled (FIG. 8A) and isotopically labeled CEdG diasteromers (FIGS. 8B-8C).
Figure 8:
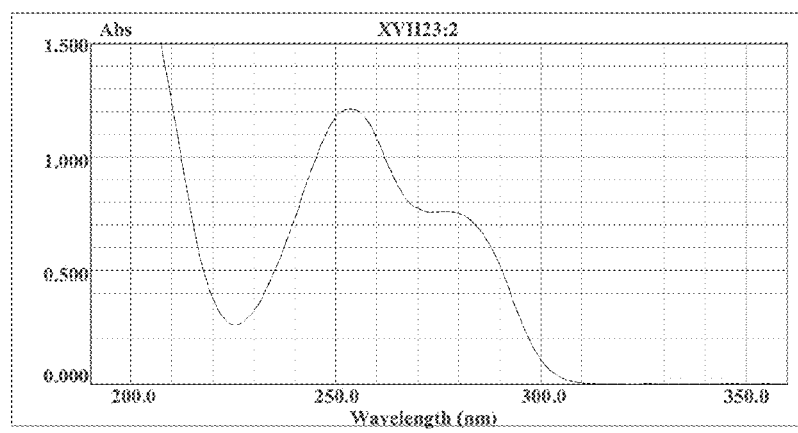
Figure 8:
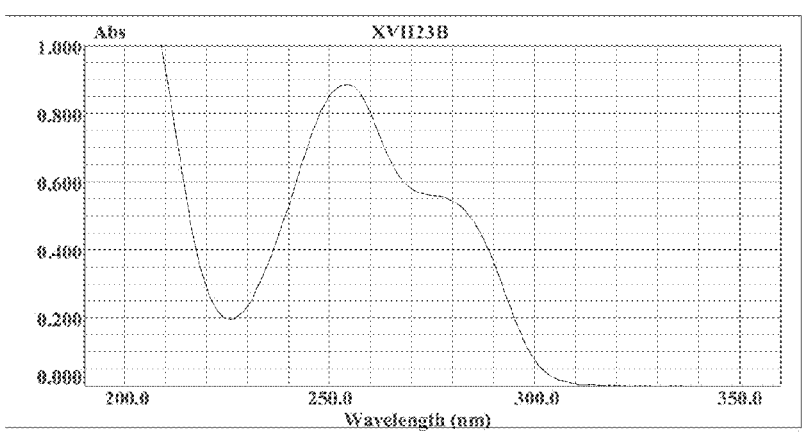
Figure 9:
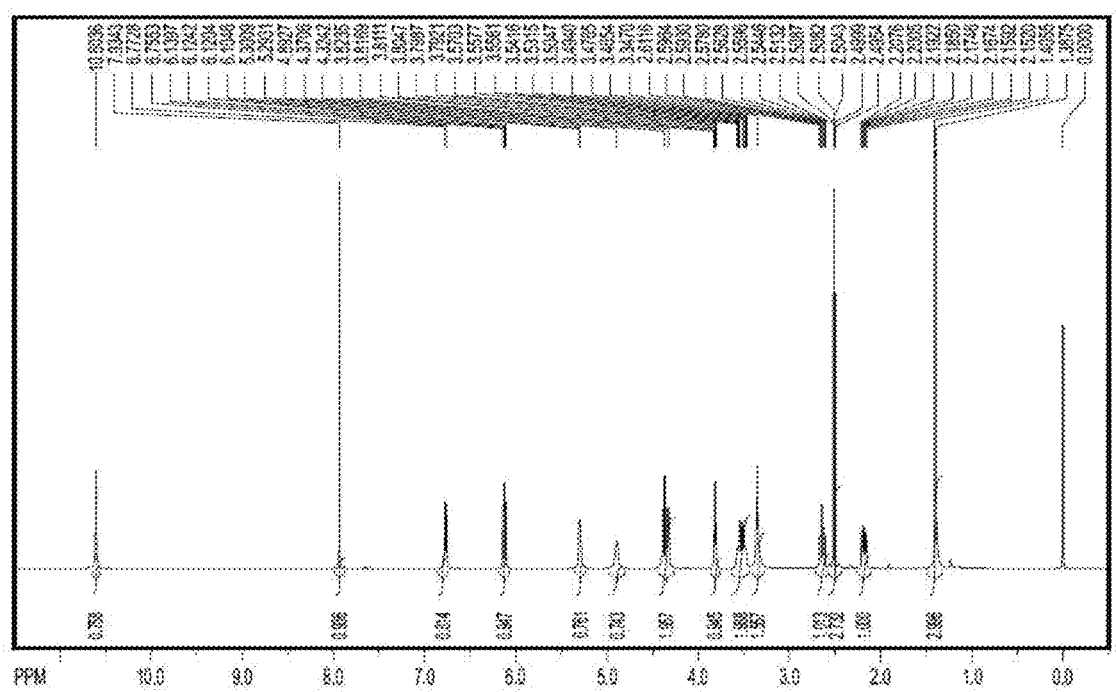
FIG. 9. Proton ($^1$H) NMR of CEdG(A) isomer. The following parameters apply to the spectrum: transmitter freq: 399.806855 MHz; time domain size: 21340 points; width 5208.33 Hz=13.027115 ppm=0.244064 Hz/pt; number of scans: 512; freq. of 0 ppm: 399.804642 MHz; processed size: 65536 complex points; LB: 0.00; GB: 0.00.
Figure 10:
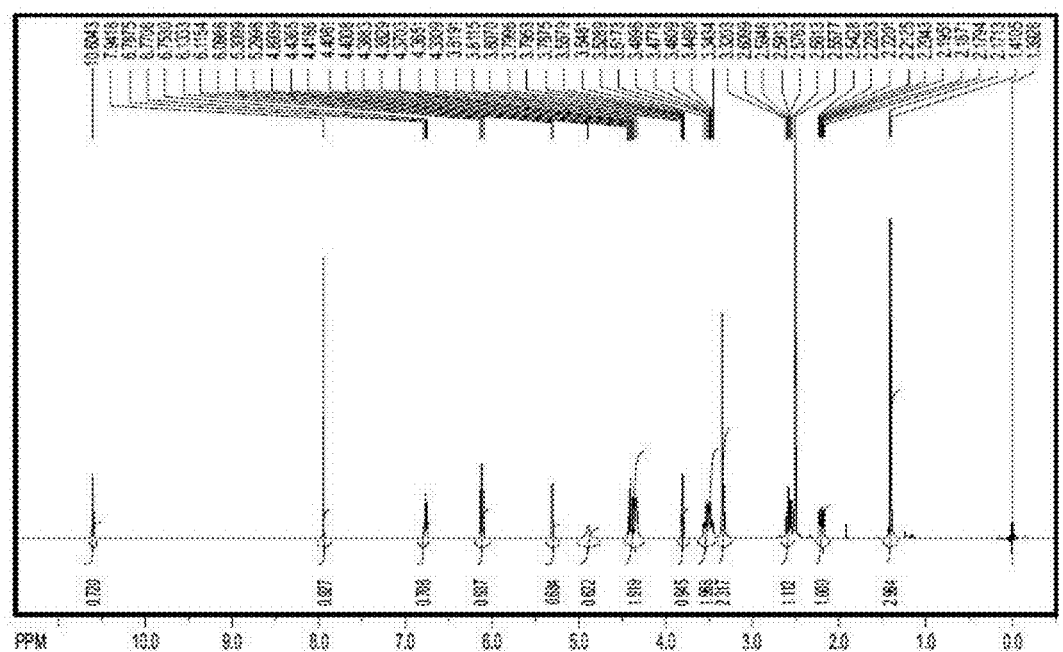
FIG. 10. Proton ($^1$H)NMR of CEdG(B) isomer. The following parameters apply to the spectrum: transmitter freq: 399.806855 MHz; time domain size: 21340 points; width 5208.33 Hz=13.027115 ppm=0.244064 Hz/pt; number of scans: 512; freq. of 0 ppm: 399.804643 MHz; processed size: 65536 complex points; LB: 0.500; GB: 0.00.
Figure 11:
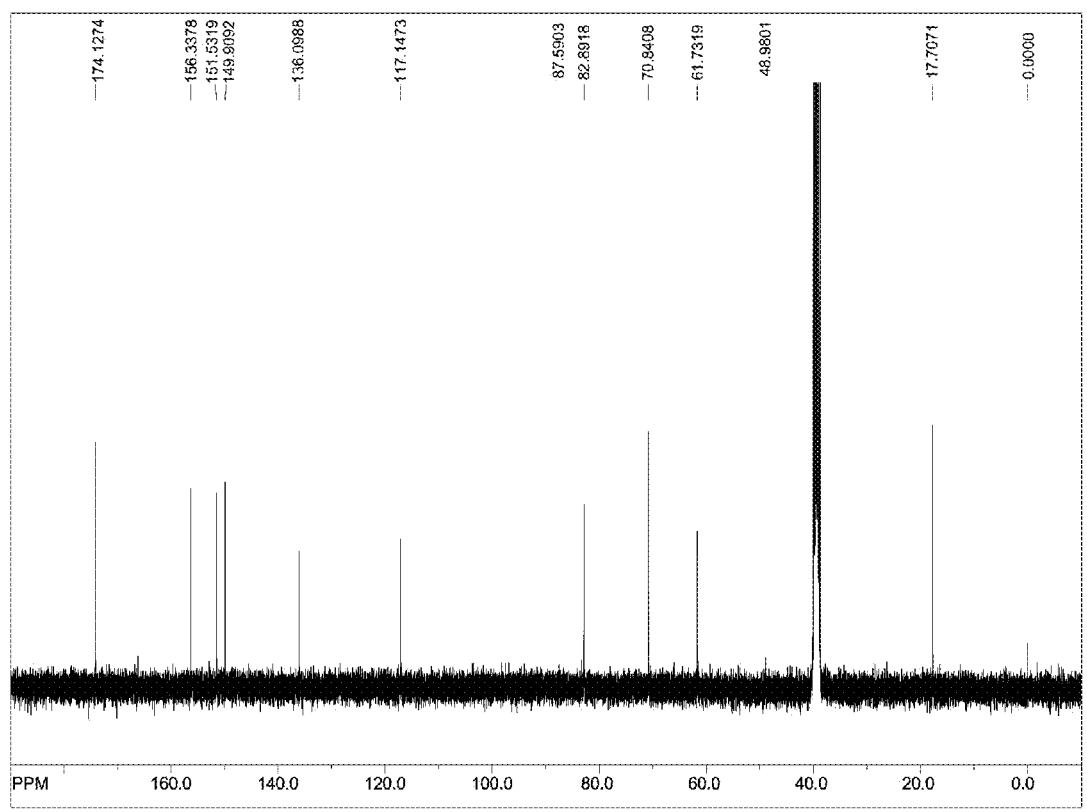
FIG. 11. Carbon data: $^{13}$C NMR of CEdG(A). The following parameters apply to the spectrum: transmitter freq: 100.541493 MHz; time domain size: 63750 points; width 24509.80 Hz=243.778000 ppm=0.384468 Hz/pt; number of scans: 12000; freq. of 0 ppm: 100.531015 MHz; processed size: 65536 complex points; LB: 0.00; GB: 0.00.
Figure 12:
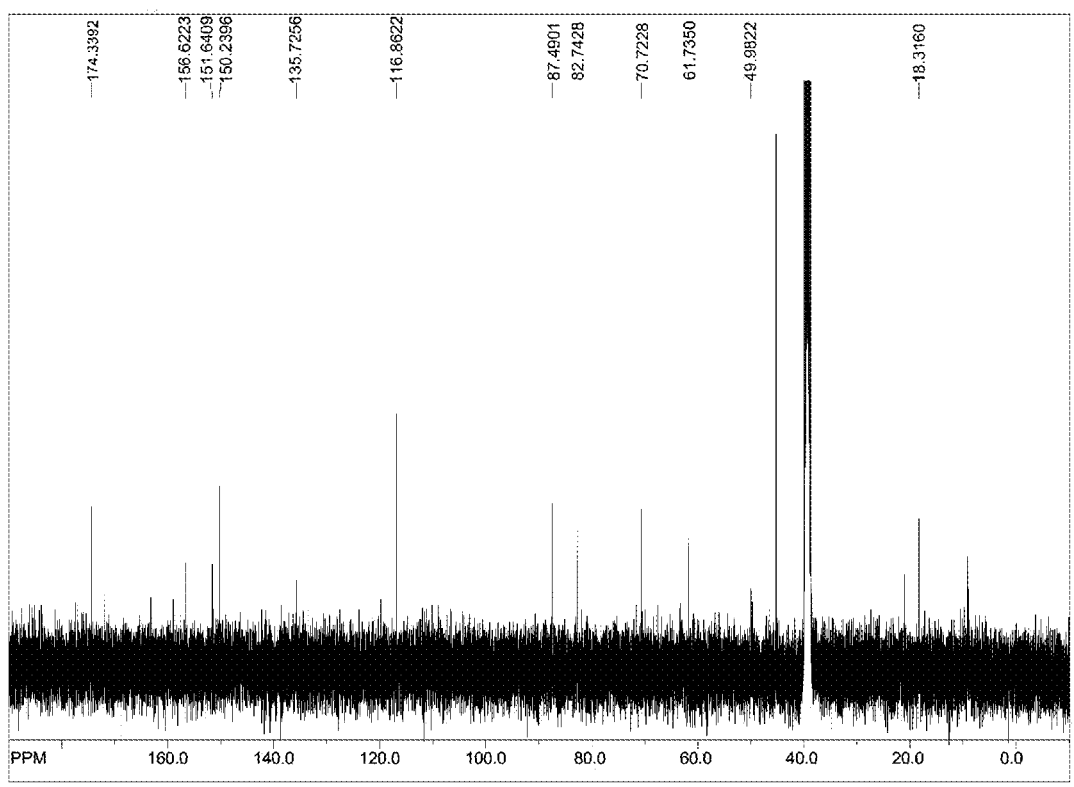
FIG. 12. Carbon data:$^{13}$C NMR of CEdG(B). The following parameters apply to the spectrum: transmitter freq: 100.541493 MHz; time domain size: 63750 points; width 24509.80 Hz=243.778000 ppm=0.384468 Hz/pt; number of scans: 27000; freq. of 0 ppm: 100.531015 MHz; processed size: 65536 complex points; LB: 0.500; GB: 0.00.
Figure 13:
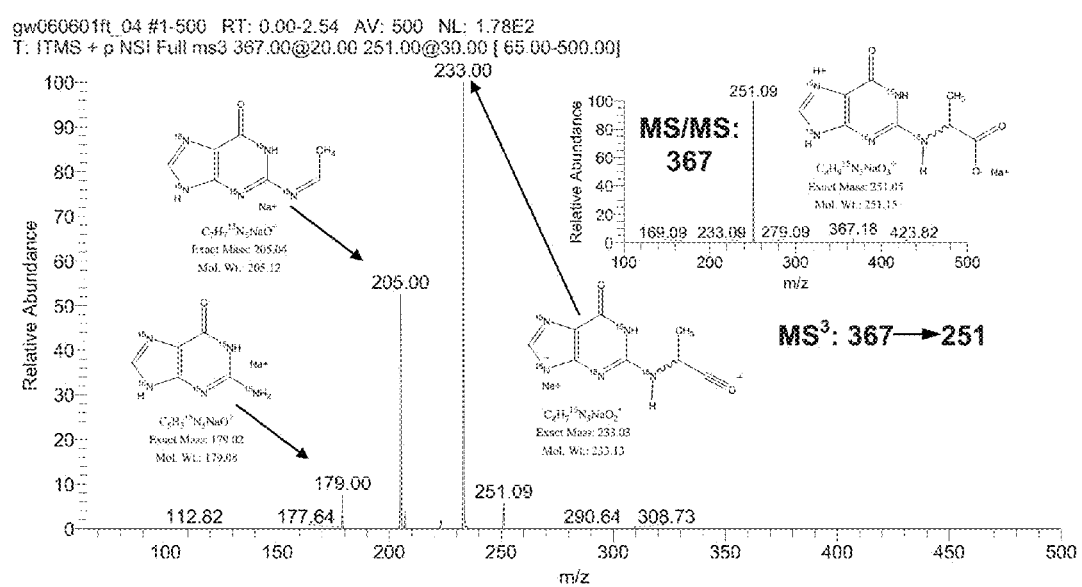
FIG. 13. MS2 and MS3 of sodiated CEdG(A) parent ion obtained using the Thermo Finnigan LTQ-FT linear ion trap mass spectrometer, showing the expected molecular fragments for the isotopically enriched standards.
Figure 14A:
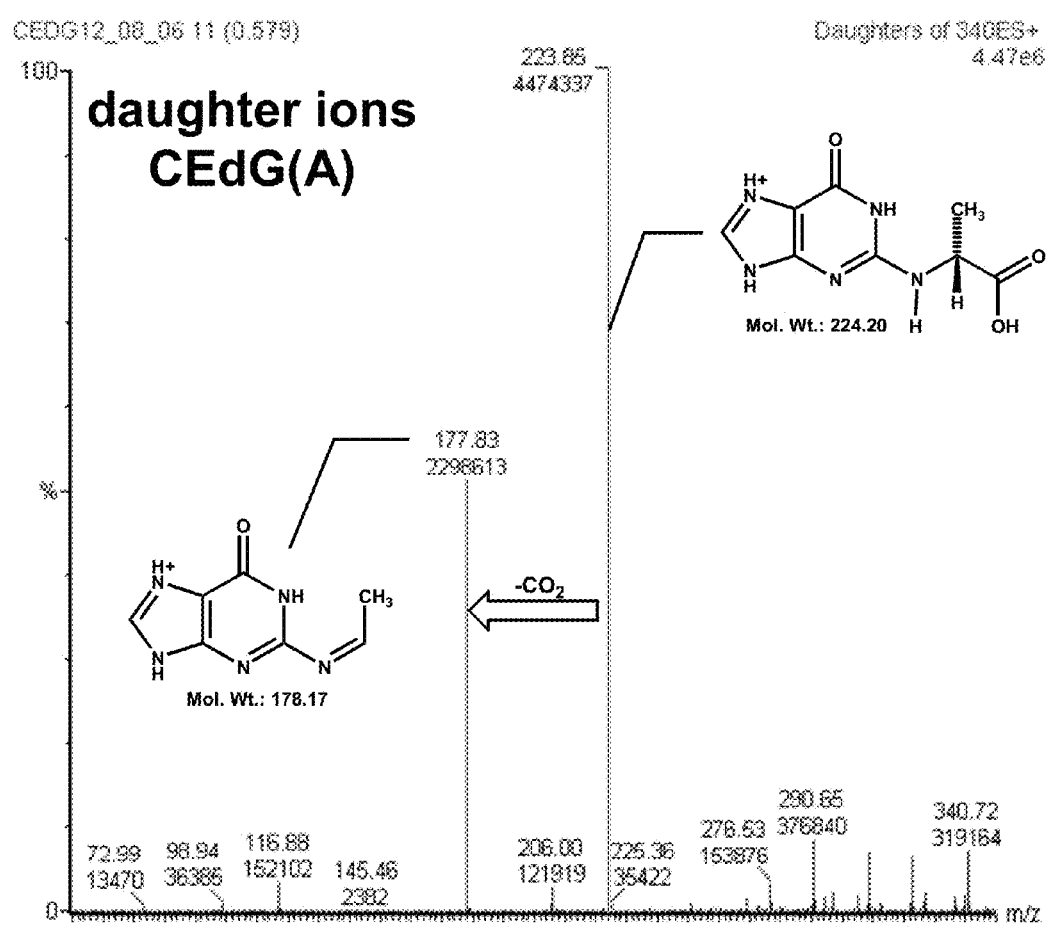
FIGS. 14A and B. Product ion scans for CEdG(A) (FIG. 14A) and $^{15}$N$_5$-CEdG(A) (FIG. 14B) at m/z 340 and 345, respectively, showing the daughter ions at m/z 224 and 229 monitored using a Micromass Quattro Ultima Triple Quadrupole Mass Spectrometer, showing the expected molecular fragments for the isotopically enriched standards.
Figure 14B:
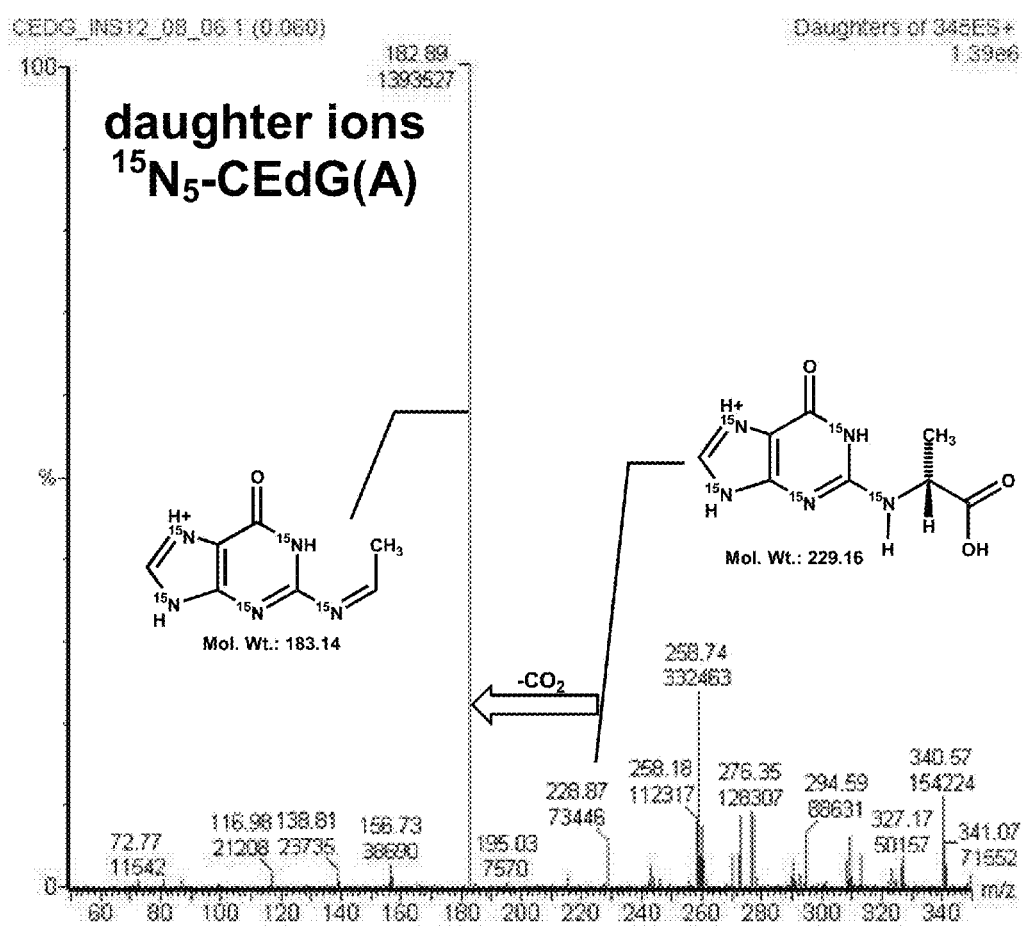
Figure 15:
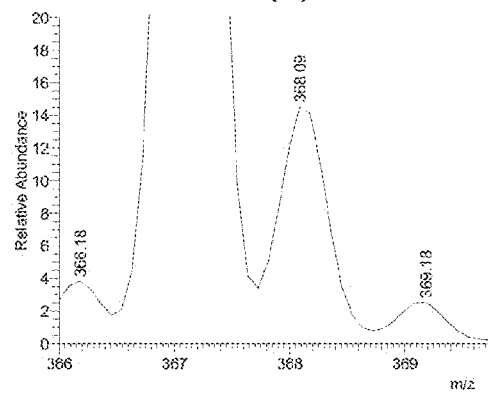
FIG. 15. Observed isotopic distributions for $^{15}$N$_5$-CEdG (A) (FIG. 15A) and $^{15}$N$_5$-CEdG(B) and the calculated isotopic distribution for $C_{13}H_{17}{}^{15}N_5NaO_6$ (FIG. 15B) The latter was calculated using the Molecular Weight Calculator, V. 6.38 (FIG. 15C).
Figure 15:
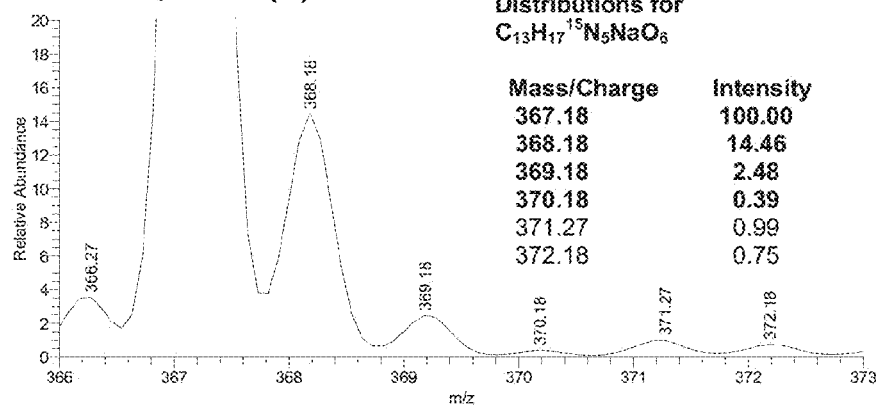
Figure 15:
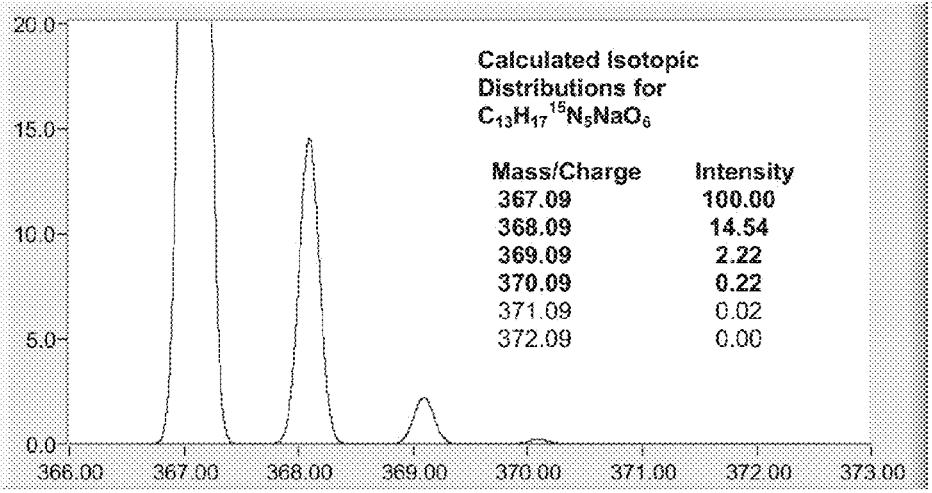

Fractions were lyophilized to dryness prior to resuspension in 18.2 MΩ $H_2O$. Concentrations of stock solutions were calculated by UV using a molar extinction coefficient of 12,300 @255 nm. See, for example, FIG. 8. Mass analyses of $^{15}N_5$-CEdG diastereomers were conducted using a Thermo-Finnigan LTQ FT ion trap mass spectrometer in the positive ion mode. A full scan MS for CEdG-A is shown in FIG. 3. The most intense ion was observed for the sodiated peak, $C_{13}H_{17}{}^{15}N_5NaO_6{}^+$: m/z 367.18 (obs), m/z 367.09 (calc). $^1$H NMR assignments for CEdG-A: $^1$H NMR (400 MHz, $d_6$-DMSO, 18° C.) δ 10.60 (s, 1H, N1-H̲), δ 7.93 (s, 1H, C8-H̲), δ 6.76 (d, 1H, C2-NH̲), δ 6.12 (dd, 1H, C1'-H̲), δ 5.30 (d, 1H, C3'-OH̲), δ 4.89 (vbr, 1H, C5'-OH̲), δ 4.36 (m, 1H, C2-NH—CH̲), δ 4.32 (m, 1H, C4'-H̲), δ 3.81 (m, 1H, C3'-H̲), δ 3.50 (ddd, 2H, C5'-H̲$_2$), δ 2.64 (ddd, 1H, C2'-H̲), δ 2.18 (ddd, 1H, C2'-H̲), δ 1.39 (d, 3H, C2-NH—CH—C H̲$_3$). $^{13}$C NMR assignments for CEdG-A: (100.5 MHz, $d_6$-DMSO, 18° C.) δ 174.1 (C2-NH—CH—C̲OON), δ 156.3 (C6), δ 151.5 (C2), δ 149.9 (C4), δ 136.1 (C8), δ 117.1 (C5), δ 87.6 (C3'), δ 82.9 (C1'), δ 70.8 (C4'), δ 61.7 (C5'), δ 49.0 (C2-NH—C̲H), δ ~39.5 (C2'), δ 17.7 (C2-NH—CH—C̲H$_3$). $^1$H and $^{13}$C NMR assignments for CEdG-B are nearly identical to the A isomer.

Synthesis of Oligonucleotides Containing Site-Specifically Modified CEdG Residues.

A synthetic scheme was devised for the quantitative preparation of oligonucleotides containing CEdG that can be readily accommodated on any standard DNA synthesizer using the conventional phosphoramidite technology. Oligos containing only pure D or L CEdG were prepared in a stereochemically pure manner using D or L alanine in a reaction that proceeds with retention of configuration. A NPE protected 2-fluoropurine phosphoramidite derivative was introduced into the polymer during standard oligonucleotide synthesis, and the reaction with D or L alanine was carried out prior to any deprotection step.

Specifically, stereochemically pure (R) or (S) CEdG oligonucleotides were synthesized by nucleophilic substitution with either (R) or (S) alanine on 2-fluorodeoxyinosine (2-FdI) containing oligos followed by deprotection and purification. Oligonucleotides were prepared using an ABI394 DNA synthesizer loaded with either standard or 2-F-dI-CE phosphoramidites (0.2 μM scale). For the preparation of CEdG containing oligonucleotides, F-dI-containing fully-protected oligomers still bound to the CPG support were suspended in an aqueous solution of 1M D- or L-alanine in 250 mM potassium carbonate at 50° C. for 40 hours. Complete removal of all protecting groups was achieved by extended reaction at 50° C. in concentrated ammonia for 7 days. Separation of the desired oligonucleotide from failure sequences and other impurities was achieved by ion-pairing chromatography on a 10 mm×250 mm×Bridge Prep C18 5 μm column (Waters, Milford, Mass.), using a 40 minute 9.0% to 9.5% gradient of acetonitrile vs 100 mM triethylammonium acetate (TEAA, Fluka, Milwaukee, Wis.) at a constant 45° C. All oligonucleotides were characterized by rechromatography under the indicated conditions and analyzed by ESI-FT/MS on an LTQ-FT (Thermo-Finnigan, San Jose, Calif.) in the Mass Spectrometry Core of the City of Hope Cancer Center.

Figure 16:
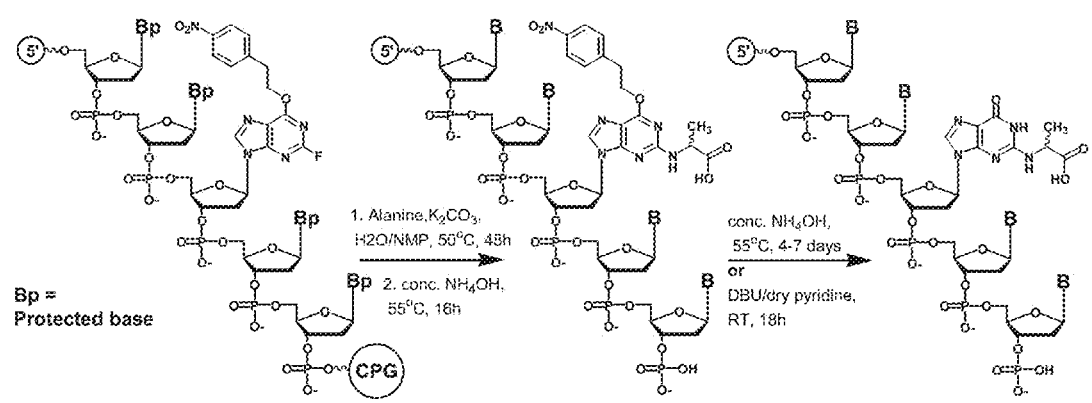
FIG. 16. Synthesis of oligonucleotides containing site-specifically modified CEdGs.
Figure 17:
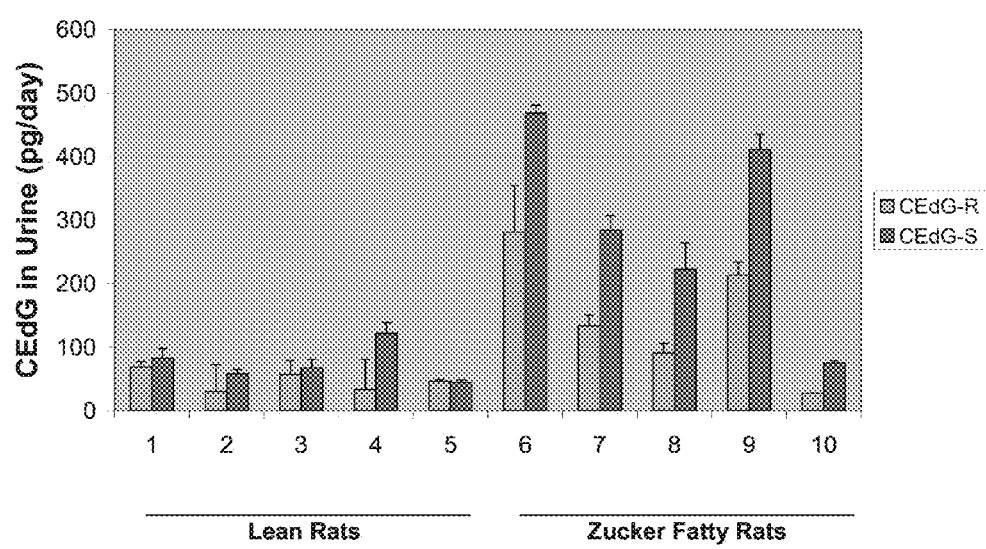
FIG. 17. Consistent elevation of CEdG in obese rats, nearly 10-fold in some examples, relative to lean controls. There is consistently more (S) isomer relative to (R) in biological samples from both rodents and humans.

This new synthesis is superior to previously known syntheses for CEdG because it allows for the preparation of oligos containing stereochemically pure (R) or (S) CEdG in high yield. Oligos containing uniquely substituted CEdG residues are used to calibrate the biological measurement of CEdG by serving as internal standards. They are also used in biochemical assays for examining the biological consequences of site-specific CEdG substitution in DNA, including, but not limited to, aspects of their repair and mutagenic potential (FIG. 16). This synthetic scheme may also be used to make site specific substitutions for other AGEs.

Stable Isotope Dilution.

Internal standards for other AGEs are usually contain stable isotopes (15N, 13C, 18O) to create a different pass from the related analyte. Different concentrations of the stable isotope substituted compounds are prepared and analyzed by MS in order to determine the response height of the ion current as a function of different concentrations. A calibration plot is made of concentration vs ion current response. This is typically a linear plot of concentrations ranging from anticipated lowest detectable amounts to highest expected. The ion current response increases with concentration. To measure CEdG in a biological sample, a known amount of stable isotope standard is "spiked" into the sample. Since the CEdG in the sample and the CEdG standard have different molecular weights, they can be resolved by MS. The ion current response of the CEdG in the sample is compared to the response of the spiked istopically enriched CEdG. Since the concentration of isotopically enriched standard in the sample is known, comparison allows for calculation of the amount of CEdG in the biological sample by fitting to the calibration plot.

Stability Studies of CEdG in Acidic Solution.

A 1.25 mM solution of CEdG-A, B or dG in 100 μL of 1M AcOH (pH 2.4) was stirred at 37° C. 10 μl aliquots were removed periodically and added to 40 μL of 2M TEAA (pH 7.0). HPLC product analyses were performed using an Alltech HS HyperPrep 100 BDS C18 8μ column. A gradient of 0 to 4% $CH_3CN$ over 5 min was followed by 6.5% $CH_3CN$ over 30 min. TEAA (pH 7) was kept constant at 50 mM. The ratio of free base (CEG or G) to intact nucleoside (CEdG or dG) was calculated by integration of the corresponding HPLC peaks (see inset in FIG. 4). The CEG free base was identified as Peak A by ESI-MS in the negative ion mode. $C_8H_8O_3N_5$, observed: m/z 222.064; calculated: m/z 222.063.

Animal Studies.

Figure 5:
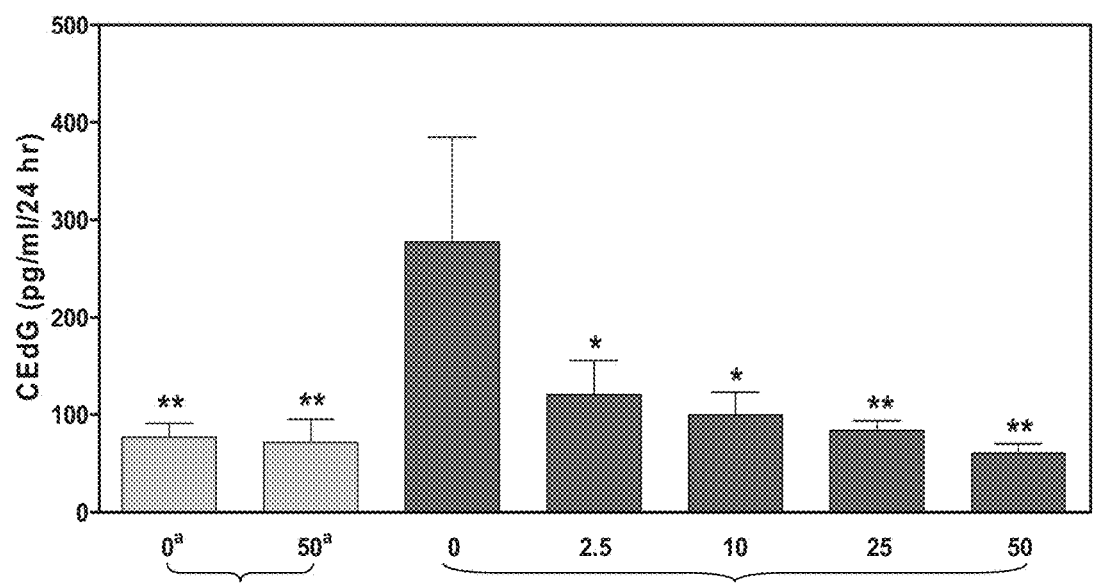
FIG. 5. Quantitation of CEdG in normal (light grey) and diabetic (dark grey) Sprague-Dawley rats. Superscript a ("$^a$"): Ordinate values represent ad libitum concentrations of the AGE inhibitor drug LR-90 (mg/L). *$P<0.05$ and **$P<0.01$ vs untreated diabetic animals (Bonferonni's test) (no asterisks).

All animal studies were carried out in compliance with the policies outlined in NIH Publication No. 85-23 "Guide for the Care and Use of Laboratory Animals." Male Sprague-Dawley rats were rendered diabetic by injection of streptozoticin and maintained as previously described.[18] The AGE inhibitor LR-90 was administered ad libitum at concentrations ranging from 2.5-50 mg/L. Rats were housed in metabolic cages and urine was collected over a 24 hour period with several drops of toluene to inhibit microbial growth. Urine samples were stored at −80° C. prior to LC-MS/MS analysis for CEdG. The data in FIG. 5 represent 3 replicates from n different animals: non-diabetic controls, n=6; non-diabetic treated with 50 mg/L LR-90, n=5; diabetic control, n=3. For diabetic rats treated with varying doses of LR-90: 2.5 mg/L, n=4; 10 mg/L, n=5; 25 mg/L, n=6; 50 mg/L, n=8.

Urine Sample Preparation.

CEdG was concentrated from urine by solid phase extraction. A 1 ml strata-X-C cartridge was pre-conditioned by the sequential addition of 1 ml MeOH/$CH_3CN$ (1:1) followed by 2×1 ml 2% $H_3PO_4$. Then $^{15}N_5$-CEdG was added as an internal standard (final concentration 5 μg/ml), the sample was acidified with 10 μl of 86% $H_3PO_4$, and finally 0.4 mL of urine was introduced via suction filtration. The cartridge was then washed with sequential additions of 1 ml 0.1% $H_3PO_4$ and 1 ml MeOH and then dried under vacuum for 1 minute. Finally, CEdG and $^{15}N_5$-CEdG containing fractions were eluted from the cartridge with 1 mL 3% $NH_4OH$ in MeOH:$CH_3CN$ (2:8 v/v). The eluent was evaporated to dryness in a centrifugal concentrator and reconstituted with 200 μl 0.1% formic acid prior to LC-MS/MS injection.

Preparation of Mononucleosides from DNA.

Calf thymus or tissue-extracted DNA (100 μg) was dissolved in 80 μL of autoclaved 18.2 MΩ $H_2O$ containing 20 μL of sodium acetate (100 mM, pH 5.5), 20 μL of 1×TBE, 1.5 μL of 50 mM $ZnCl_2$, and 2.37 μL of a 100 mM AG or D-P stock solution. DNA was denatured at 95° C. for 5 min on a PCR heating block and then brought to 4° C. for 5 min. After equilibration to 45° C., 1.5 μL of 10 U/μL nuclease P1 was added. Alkaline phosphatase (4 μL of 8 U/μL), 1 U of bovine phosphodiesterase, and 14 μL of 100 mM $CaCl_2$ were added after 1 hour, and the hydrolysis/dephosphorylation was continued for another 7 hours. DNA concentrations were determined by UV spectroscopy (1 $OD_{260}$=50 μg/ml) and samples were stored at −80° C. prior to MS analyses. A 5 μL aliquot of digest was diluted to 200 μL and used for quantitation of 2-deoxyguanosine by HPLC integration using a Beckman C-18 reverse phase (25 cm×4.6 mm) column (Fullerton, Calif.). Separation was achieved isocratically using a mobile phase of 6% MeOH, 0.1% acetic acid in water.

DNA Isolation from Human Tissue.

Breast tumor and adjacent normal tissue was obtained from the frozen tumor bank of the City of Hope Pathology Core. A pea-sized section (~100 mg) of tissue was minced and suspended in 1.2 mL of digestion buffer (100 mM NaCl, 10 mM Tris HCl, pH 8, 25 mM EDTA, pH 8, 0.5% SDS, 0.2 mg/mL proteinase K, 10 mM D-penicillamine) and incubated at 50° C. in a water bath for 12-18 h. DNA was then extracted using an equivalent volume of phenol/chloroform/isoamyl alcohol (25:24:1). The aqueous fraction was separated and 0.5 volumes of ammonium acetate and 2 volumes of 100% ethanol were added. The DNA was spooled, washed twice with 70% ethanol, pelleted, and resuspended in autoclaved 18.2 MΩ water. The enzymatic hydrolysis was carried out as described above.

LC-ESI-MS/MS.

Quantification of CEdG was performed using a LC-MS/MS method. Measurement of 8-oxo-dG was performed as previously described.[19] CEdG and $^{15}N_5$-CEdG (internal standard) were synthesized and purified. Measurements were performed using an Agilent 1100 Capillary LC system (Agilent Technologies, Palo Alto, Calif.) in line with a Micromass Quattro Ultima Triple Quadrupole Mass Spectrometer (Micromass, Beverly, Mass.) operating in positive-ion mode. The detector settings were as follows: capillary voltage, 3.5 kV; cone voltage, 18 V; collision cell voltage, 11 V; source temperature, 350° C.; desolvation temperature, 150° C.; cone gas flow, 620 liter/h; and desolvation gas flow, 500 liter/h. The mass transitions monitored for CEdG and $^{15}N_5$-CEdG were 340.3→224.3 and 345.4→229.4 respectively. HPLC was accomplished using isocratic conditions with a mobile phase of 15% aqueous MeOH with 0.1% formic acid on a Prodigy ODS C-18 (25 cm×2.0 mm×5 micron) column (Phenomenex, Torrance, Calif.). The flow rate was 0.2 ml/min with a total run time of 30 min. The retention times for CEdG diastereomers A and B using these conditions were 9.3 and 16 min, respectively. The lower limit of quantitation for CEdG, defined as a peak height of ≥5× baseline noise, was 0.1 ng/ml in the starting solution or 0.2 pg on column.

For urine analyses and calf thymus DNA digests, calibration curves were constructed using 0.75, 1.5, 3, 6, 12, 24, and 48 ng/mL of synthetic CEdG in urine or in blank nucleoside digestion buffer. For human breast tissues, CEdG concentrations used for calibration were 0.19, 0.38, 0.75, 1.5, 3, and 6 ng/mL. Linearity of the calibration curves were demonstrated with R-squared values of ≥0.996. Inter- and intra-day accuracy of the assay across the range of the standard curve was established to be 96% and 94% of target concentrations, respectively. The assay was also determined to be unbiased with both inter- and intra-day precision within ±6%. Quantification of 2'-deoxyguanosine (dG) was performed by HPLC integration of DNA digests and final values were expressed as CEdG/$10^7$dG.

Urine extracts or mononucleoside digests were spiked with 20 μL of 100 ng/mL $^{15}N_5$-labeled CEdG and 10 μL of 86% phosphoric acid. Samples were then loaded onto strata-X-C cation mixed mode columns that had been pre-conditioned with MeOH/$CH_3CN$ (1:4) followed by 2% phosphoric acid. After sample loading, columns were washed with 0.1% phosphoric acid, followed by MeOH. Nucleosides were eluted with 3% ammonium hydroxide in MeOH/$CH_3CN$ (1:4) and evaporated to dryness in a centrifugal concentrator. Samples were reconstituted with 100 μL of 0.1% formic acid and analyzed directly by LC-MS/MS. Recovery of CEdG diastereomers and $^{15}N_5$-CEdG from urine and mononucleoside digests was determined to be 85+/−0.9%.

Synthesis and Characterization of CEdG Isotopomers.

Isotopomers of CEdG were prepared by a modification of the method of Ochs and Severin.[17] Reaction of $^{15}N_5$-dG with (dl)-glyceraldehyde in phosphate buffer afforded the desired products as a ~1:1 mixture of diastereomers in ~60% yield. Unenriched CEdG diasteromers were prepared in an analogous manner. The $N^2$ amino group of dG catalyzes the dehydration of glyceraldehyde to yield the hemiacetal of MG in situ, which then reacts to provide CEdG either directly by condensation at $N^2$ or alternatively via the rearrangement of an intermediate $N^1$, $N^2$ cyclic diol. The two diastereomers of CEdG were readily resolved by HPLC and eluted at 24 and 29 minutes (FIG. 2) on a $C_{18}$ reverse phase column. In spite of significant differences in chromatographic retention times, both the proton and carbon NMR spectra for CEdG-A and B were essentially superimposable, with the chemical shift differential on the order of <0.1 ppm for proton and <1.0 ppm for carbon.

Mass analyses of the CEdG isotopomers were performed using a Thermo Finnigan LTQ ion trap mass spectrometer in the positive ion mode. The most intense signal in the parent ion spectrum of the isotopically enriched standard corresponded to the sodium salt of $^{15}N_5$-CEdG at m/z 367 $[PNaH]^+$ (FIG. 3). The disodium salt $[PNa_2]^+$ and the dihydro adduct $[PH_2]^+$ were also observed at m/z 389 and 345, respectively. Collision induced dissociation of the m/z 367 parent ion gave rise primarily to the sodiated base ion $[BNaH]^+$ at m/z 251. The observed isotopic distribution for $C_{13}H_{17}{}^{15}N_5NaO_6$ was found to be in good agreement with the calculated values.

Stability of CEdG to Acid-Catalyzed Depurination and Sidechain Isomerization.

The chemical stability of CEdG was examined as an important criterion for evaluating its suitability as a quantitative biomarker. Purified stereoisomers of synthetic CEdG were subjected to acidic conditions (1 M AcOH at 37° C.) and the extent of released free base and diastereomer interconversion was monitored by HPLC as a function of time. Analogous experiments were performed for dG and the results are presented in FIG. 4. The approximate half-lives for depurination were 750 and 500 min for the A and B isomers respectively, whereas dG was observed to be less stable, with a half-life of 440 min under these conditions. No racemization of the sidechain stereocenter was detected during acidic hydrolysis, i.e., no interconversion of CEdG isomers A and B was observed.

Urinary CEdG Measurement in Diabetic Rats.

A diabetic animal model was used to examine the relationship between glycemic status and CEdG levels. Rats rendered diabetic by streptozoticin (STZ) treatment possess elevated MG relative to normal controls and thus appeared likely to exhibit an increased burden of CEdG adducts. The effect of AGE inhibitor, LR-90, was also examined. The results of these experiments are shown in FIG. 5. Analyses of urine from non-diabetic control animals collected over a 24 hr period revealed mean CEdG levels of 77 µg/ml (FIG. 5). The induction of diabetes increased the level of excreted CEdG by ~4 fold. Administration of LR-90 to diabetic rats ad libitum at a dose corresponding to 2.5 mg/L resulted in a 2.3 fold decrease in CEdG titer. Increasing concentrations of LR-90 led to a dose dependent reduction in CEdG, and at 25 mg/L the adduct level in urine was comparable to that of non-diabetic animals. In contrast, administration of LR-90 at doses up to 50 mg/L in normal controls had no significant effect on CEdG levels. 8-oxo-dG was also measured as an indicator of oxidative stress in normal and diabetic rats; however, excreted 8-oxo-dG in diabetic animals was not statistically different (P>0.05) from controls.

CEdG in Organs of Zucker Fatty Rats.

Figure 18:
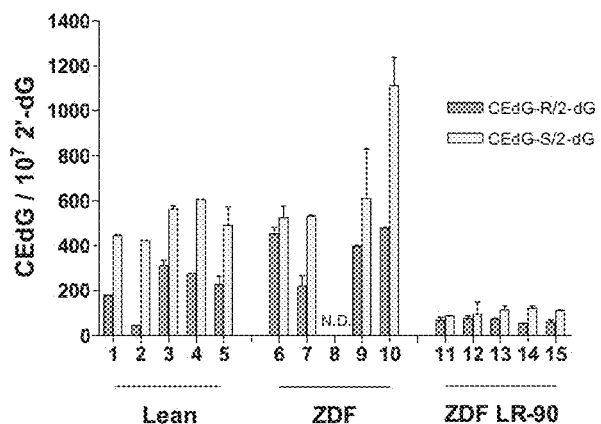
FIG. 18. CEdG levels from tissue-extracted DNA in the liver (FIG. 18A), pancreas (FIG. 18B) and kidney (FIG. 18C) of Zucker rats, lean controls and Zucker rats treated with the glycation inhibitor LR-90.
Figure 18:
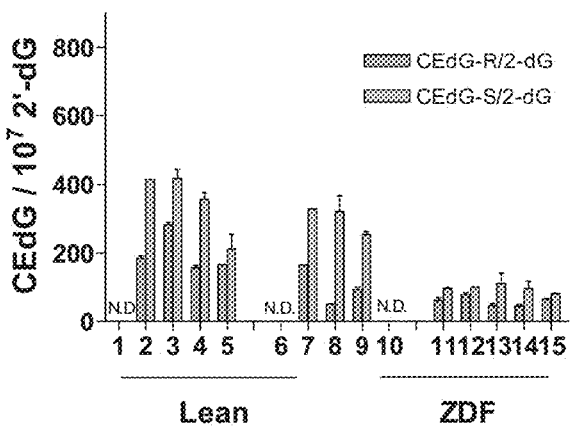
Figure 18:
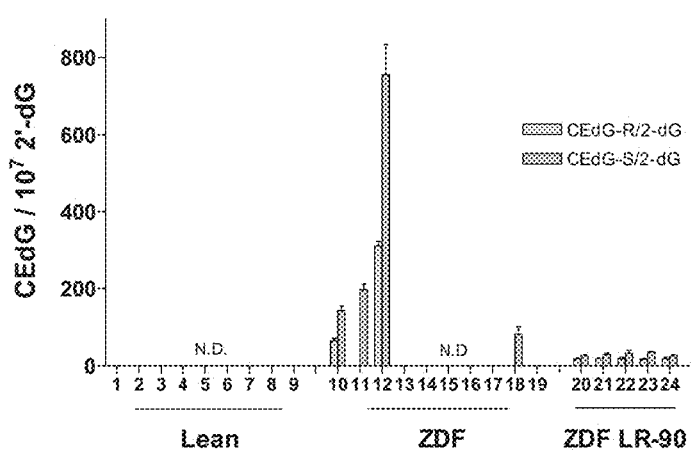

The Zucker rat is a morbidly obese, hyperinsulinemic model for Type 2 diabetes resulting from homozygous knockout of the leptin receptor. In order to determine whether elevated circulating glucose in the Zucker rat correlates with increased tissue DNA glycation, CEdG levels from tissue-extracted DNA were measured in selected organs and compared to lean controls and to Zucker rats treated with the glycation inhibitor LR-90. Data for liver, pancreas and kidney are shown in FIG. 18. Relative to lean rats, CEdG levels were found to be elevated only in kidneys. In lean animals, CEdG was below the level of detection in 9/9 animals, whereas it was elevated in 5/9 Zucker rats. All three organs of Zucker rats had a net lowering of CEdG levels following treatment with LR-90. These data show that CEdG determination can be used to monitor tissue glycation levels in response to chemotherapy.

CEdG in Calf Thymus DNA.

Figure 6:
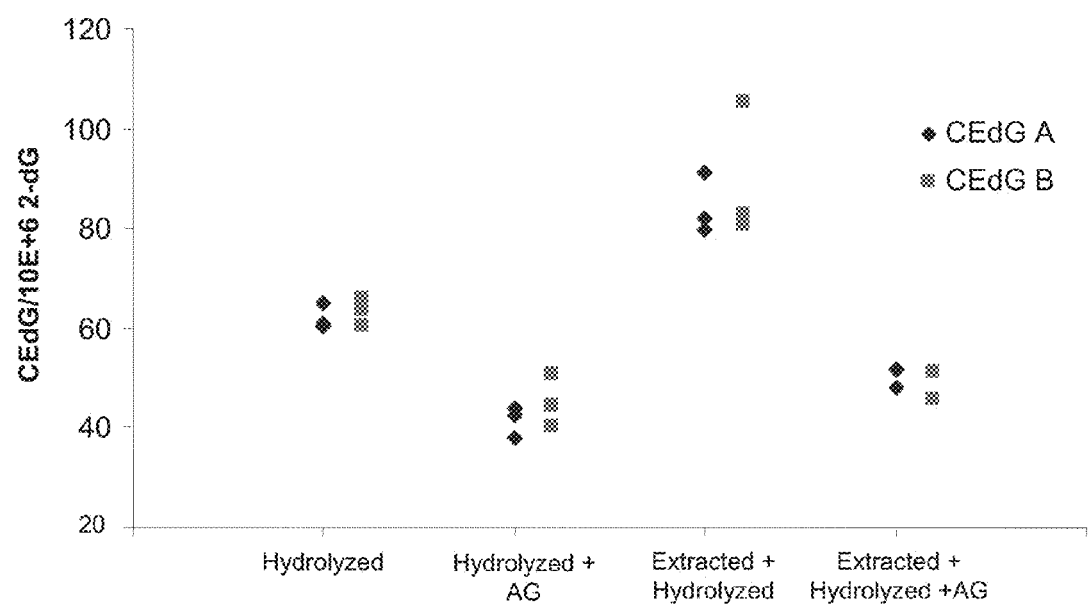
FIG. 6. LC-ESI-MS/MS measurements of CEdG diastereomers in calf thymus DNA subjected to various workup procedures. Hydrolyzed samples correspond to DNA treated with nuclease P1/alkaline phosphatase/phosphodiesterase. Calf thymus DNA samples were also reacted with proteinase K (Extracted) prior to hydrolysis. Levels of CEdG were measured in the presence or absence of carbonyl scavenger AG.

Commercial grade calf thymus DNA was used as a model substrate for developing a protocol for CEdG quantitation in double-stranded DNA. DNA was hydrolyzed and dephosphorylated by sequential addition of nuclease P1, alkaline phosphatase and phosphodiesterase. Then, mononucleosides were concentrated by solid phase extraction prior to LC-MS/MS analyses. The results of these experiments are shown in FIG. 6. Initial determinations yielded values of CEdG in the range of 60-66 CEdG/$10^6$ dG. These surprisingly high levels showed that some CEdG may have been formed artifactually during the hydrolysis and dephosphorylation. Additional CEdG may have been formed due to the release of MG from the protein reagents used in the workup during prolonged incubation. Proteins can bind MG reversibly, and up to 90% of cellular MG may be sequestered in this manner. In order to prevent additional reactions of adventitiously generated MG with DNA, carbonyl scavenging agents AG or D-P were added prior to DNA digestion and dephosphorylation. These reagents sequester MG and other alpha-oxoaldehydes by forming stable cyclic aminotriazine and thiazolidine derivatives respectively. Concentrations of AG from 0.5 to 50 mM were added prior to workup, and CEdG levels were measured in order to determine the optimal concentration required to achieve stable, reproducible levels. The addition of 10 mM AG prior to sample processing resulted in a modest but significant drop in adduct levels (45-50 CEdG/$10^6$ guanines) in calf thymus DNA, suggesting that ~15 CEdG/$10^6$ guanines were formed as a direct result of the hydrolysis and dephosphorylation protocol.

Since the extraction of DNA from biological samples requires extended reaction with proteinase K (up to 24 h), it was investigated whether this treatment could also contribute to artifactual CEdG formation. Accordingly, calf thymus DNA was subjected to mock proteolysis prior to hydrolysis and workup in the absence of carbonyl scavenger. FIG. 6 reveals an increase in adduct levels significantly higher than those observed following hydrolysis alone, with values ranging from 80-100 CEdG/$10^6$ guanines. The addition of 10 mM AG in two aliquots prior to the mock lysis treatment and hydrolysis/dephosphorylation steps resulted in a drop in measured CEdG levels comparable to that observed previously for calf thymus DNA subjected only to the hydrolysis/dephosphorylation in the presence of AG. No apparent stereoisomer bias was detected in any of these samples, i.e., the ratio of CEdGA:CEdGB was not significantly different from 1:1.

Measurement of Urinary CEdG in Post-Menopausal Women Undergoing Treatment with Aromatase Inhibitors.

Figure 19:
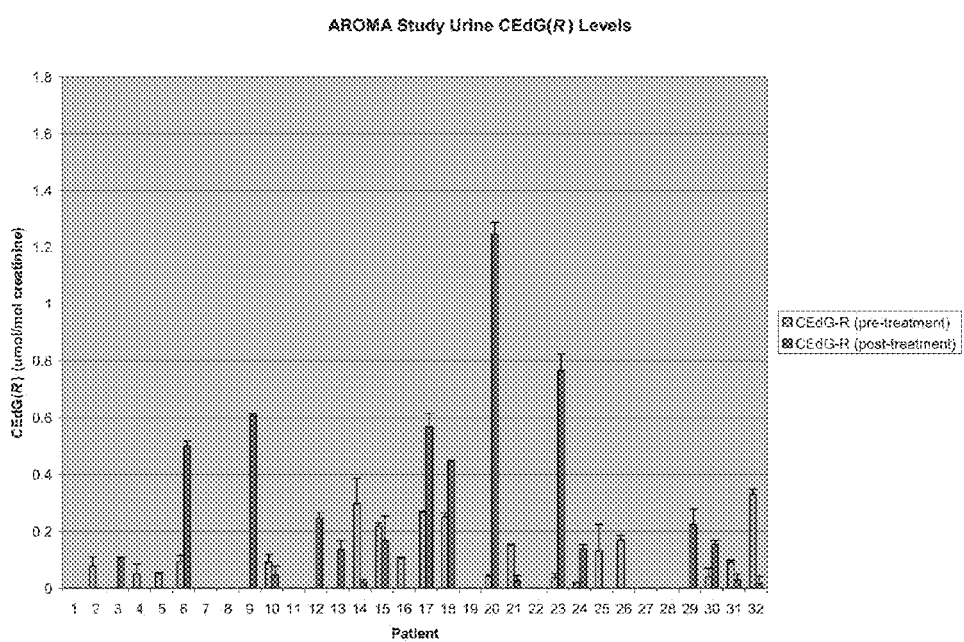
FIG. 19. Measurement of urinary CEdG(R) and CEdG(S) isomers in post-menopausal women undergoing treatment with aromatase inhibitors.
Figure 19:
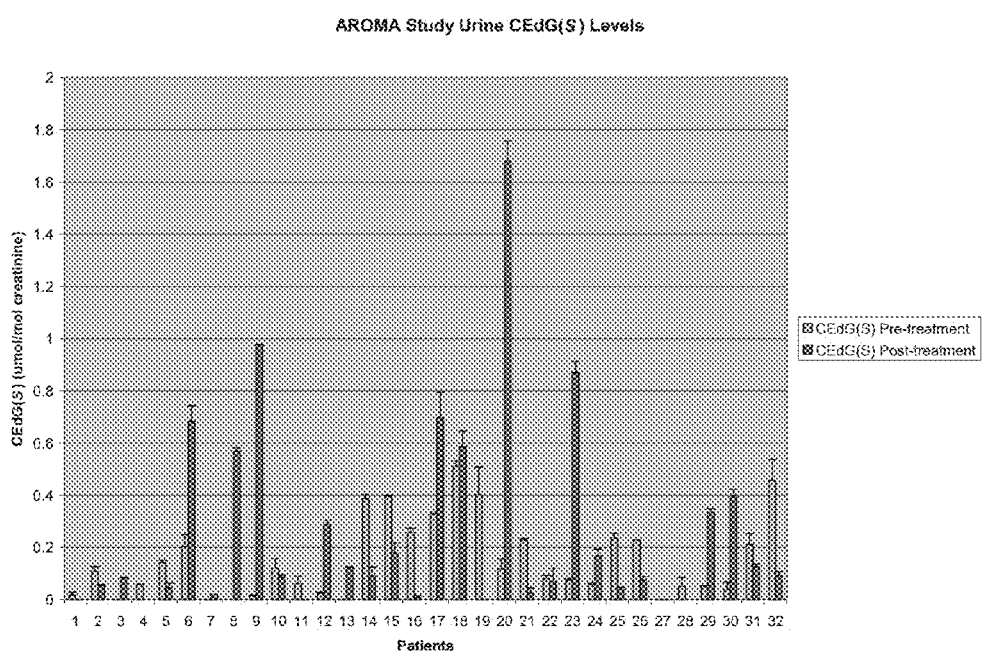

One noted side-effect of treatment with aromatase inhibitors (AI) in cancer therapy is an impairment of cognitive function, which may be linked to enhanced glycation in the brain. Enhanced brain glycation is a contributing factor in the pathology of Alzheimer's disease. In order to examine whether treatment with aromatase inhibitors can affect glycation status, urine from 32 patients was collected just prior to and 6 months following administration of AI, and levels of CEdG were measured in urine. Data for the (R) and (S) isomers of CEdG are shown in panels A and B, respectively, of FIG. 19. In the case of the (R) isomer, 12/32 patients show significantly higher levels after AI treatment, a trend also observed for 14/32 patients when levels of the (S) isomer are considered. Some of these post-treatment levels are very high, much higher than any observed pre-treatment levels. There is also good consistency between the two independent biomarkers. For example, in patients 3, 6, 9, 12, 13, 17, 18, 20, 23, 24, 29 and 30, both stereoisomers are elevated post-AI treatment. If these changes are correlated with decreased mental acuity over time, CEdG measurement can also be used to identify patients at risk for cognitive impairment. Additionally, one or more CEdG inhibitors, such as LR-90, may be administered to a subject undergoing chemotherapy in order to prevent or reduce the cognitive impairment that may accompany chemotherapy.

CEdG Measurement in Human Solid Tumors Vs Adjacent Tissue.

Figure 20:
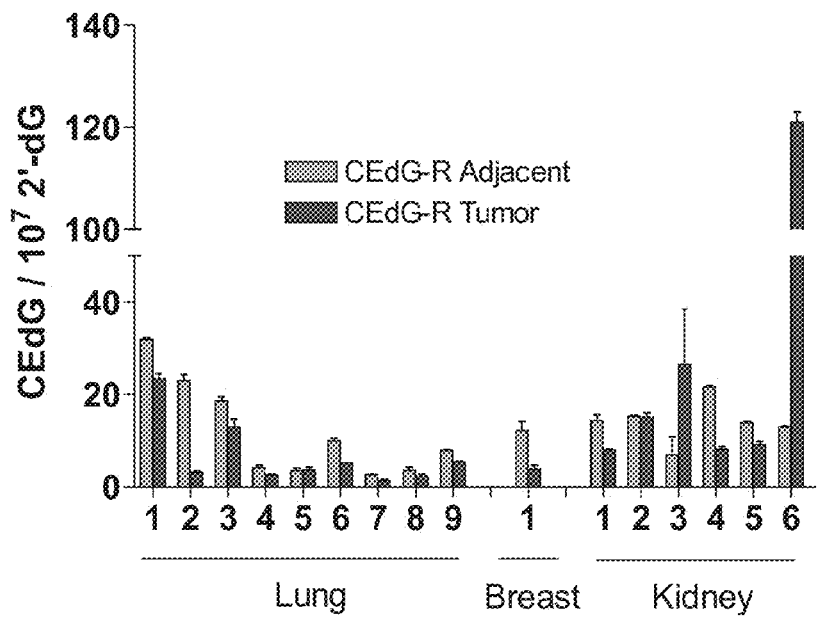
FIG. 20. CEdG(R) and CEdG(S) distribution in human solid tumors and adjacent tissue in lung, breast and kidney cancers.
Figure 20:
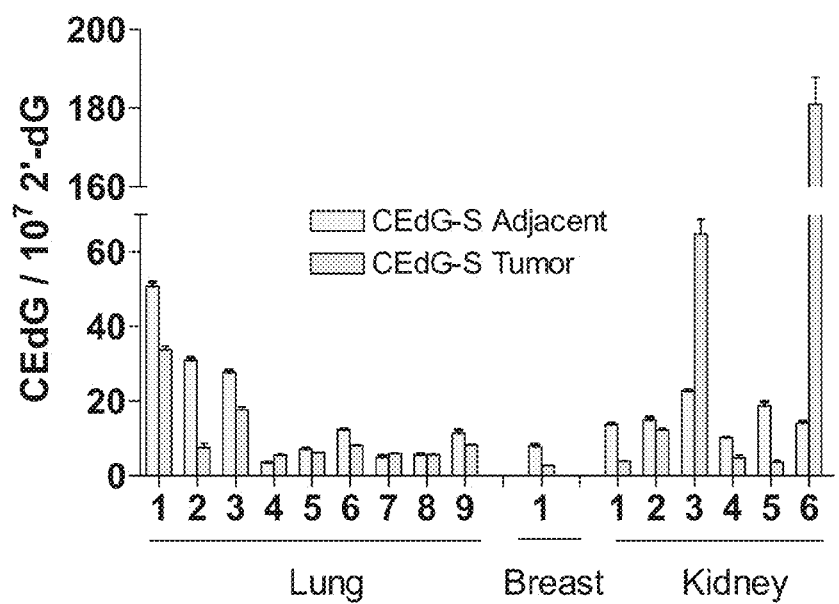

Frozen tumor specimens and adjacent tissue were obtained from the City of Hope Tumor Bank. DNA was extracted as described and analyzed for CEdG. Results are shown in FIG. 20 for (R) and (S) CEdG in lung, breast and kidney cancers. In lung cancers CEdG was observed at lower levels in tumor relative to adjacent tissue in the majority of samples. This same phenomenon was observed for the single breast cancer sample analyzed. These trends are followed for both isomers. In the case of kidney cancers, the situation is more complex, with samples 3 and 6 showing the opposite trend of higher CEdG in tumor relative to adjacent tissue. In sample 6, the levels of (R) and (S) isomers were 13 and 18 fold higher respectively in tumor relative to adjacent tissue. Other samples, such as 1, 4 and 5, follow the trend observed in the lung and breast samples.

These variations in CEdG between tumor and adjacent tissue represent the corresponding levels of glycolytic stress. In order to avoid the pro-apoptotic effects of methylglyoxal produced as a result of enhanced glycolysis, solid tumors must restrict its accumulation. Tumors with lower levels of CEdG relative to adjacent tissue, can successfully minimize their glycolytic stress in spite of maintaining elevated glycolysis. This is likely due to overexpression of the methylglyoxal scavenging enzymes glyoxalase 1 and aldose reductase in tumors, as well as enhanced removal of CEdG from DNA by repair enzymes. Tumors with elevated levels of CEdG relative to adjacent tissue are predicted to be genetically unstable, and more sensitive to chemotherapy as a result of the cytotoxic accumulation of methylglyoxal. Thus, another embodiment is a method of predicting which tumors of a cancer patient are more susceptible to chemotherapy by testing CEdG levels in tumor samples. If the CEdG levels are high, then the tumor is more likely to be receptive to chemotherapy treatment. Measurement of CEdG can also be used to identify which cancers which can benefit from targeting glyoxalase 1 and/or aldose reductase, in order to restore their sensitivity to chemotherapy. CEdG measurement can provide a direct means for identifying tumors most likely to benefit from these approaches.

Quantitation of CEdG in a Human Breast Tumor and Adjacent Normal Tissue.

Many cancer cells in the hyopoxic tumor microenvironment primarily utilize glycolysis to meet their energetic demands. This glycolytic phenotype (Warburg effect) is characterized by constitutive cell surface expression of glucose transporter proteins such as GLUT-1, and forms the basis for the diagnostic use of $^{18}$FDG-PET in the imaging of breast and other cancers.[26,27] Enhanced glycolytic flux suggests that breast tumors might exhibit abnormal levels of AGEs including CEdG. Accordingly the levels of CEdG diastereomers were measured in DNA extracted from a clinical breast tumor specimen as well as adjacent normal tissue. The data in Table 1 reveal some significant (P<0.05) differences in the levels of CEdG between tumor and normal tissue. Both stereoisomers were observed at ~3-fold higher levels in normal relative to tumor tissue (CEdG-A, P=0.02; CEdG-B, P=0.003). In the column under CEdG/107dG, "a" indicates P=0.08 versus CEdG-B in normal issue; "b" indicates P=0.02 versus CEdG-A in adjacent normal tissue; "c" indicates P=0.003 versus CEdG-B in adjacent tumor tissue; and "d" indicates P=0.03 versus CEdG-A in tumor tissue.

TABLE 1

CEdG isomers from a human breast tumor and adjacent normal tissue.

|  |  | CEdG (fmol) | dG (fmol) | CEdG/$10^7$ dG |
|---|---|---|---|---|
| CEdG-A | Normal | 234 ± 24.9 | 1.91 × $10^8$ | 12.3$^a$ ± 1.3 |
|  | Tumor | 247 ± 11.6 | 6.48 × $10^8$ | 3.9$^b$ ± 0.2 |
| CEdG-B | Normal | 151 ± 4.98 | 1.91 × $10^8$ | 7.9$^c$ ± 0.3 |
|  | Tumor | 173 ± 6.64 | 6.48 × $10^8$ | 2.7$^d$ ± 0.1 |

$^a$P = 0.08 versus CEdG-B in normal tissue.
$^b$P = 0.02 versus CEdG-A in adjacent normal tissue.
$^c$P = 0.003 versus CEdG-B in adjacent tumor tissue.
$^d$P = 0.03 versus CEdG-A in tumor tissue.

Within normal tissue, the levels of CEdG-A and B were not significantly different (P=0.08), while in tumor there was a small bias favoring CEdG-A (P=0.03). Levels of CEdG in DNA extracted from either breast tumor or adjacent tissue in the absence of carbonyl scavenger were ~1.5-2.0 fold higher; however, artifactual formation was inhibited by the addition of 10 mM D-penicillamine in two aliquots during both the cell lysis/DNA isolation and hydrolysis/dephosphorylation steps. $^{15}$N-enriched isotopomers of CEdG differing from the unlabelled adducts by 5 amu were synthesized, which provided sufficient mass resolution for accurate and reproducible quantitation using the stable isotope dilution method.

Figure 4:
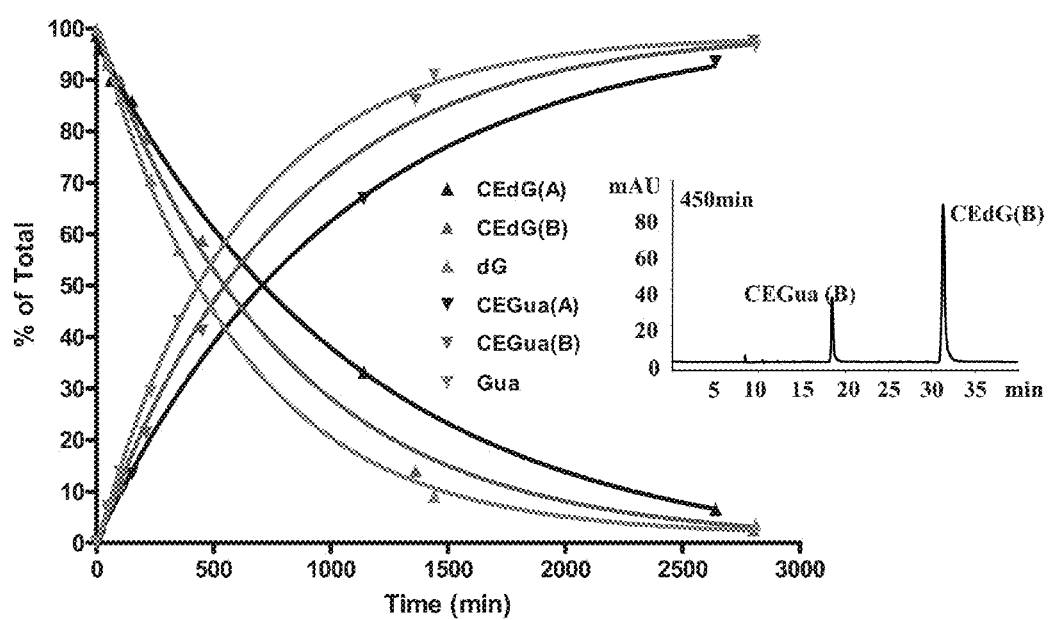
FIG. 4. Time course product profiles of the reaction of dG and the A and B stereoisomers of CEdG with 1 M AcOH at 37° C. The inset shows the HPLC chromatogram of the reaction of CEdG-B at 450 min.

The ability to simultaneously resolve and quantitate both diastereomers of CEdG provides two independent parameters for assessing DNA glycation levels within a single sample. The biological significance of the CEdG diastereomer ratio in vivo may reflect stereochemical biases in adduct repair or polymerase bypass. Of course, examination of the CEdG stereoisomer distribution in vivo by LC-ESI-MS/MS would only be meaningful if the rate of stereochemical interconversion was negligible. Regarding overall adduct stability, loss of the CEG base from either stereoisomer during workup would result in the generation of abasic sites leading to an underestimation of true nucleoside adduct levels, which was of particular concern since CEdG undergoes depurination more readily than dG at elevated temperatures. The extent of depurination and racemization was quantified by monitoring free base formation and isomer interconversion under acidic conditions at 37° C. rather than at non-physiological temperatures. FIG. 4 shows that the CEdG diastereomers possess similar stability, and are slightly more resistant to depurination under acidic conditions than dG. This fact, together with the prohibitive barrier to stereochemical interconversion, indicates that determination of CEdG diastereomer ratios may be plausibly used in quantitative biomarker studies. Various quantifications of CEdG are found in FIGS. 9-15.

Figure 7:
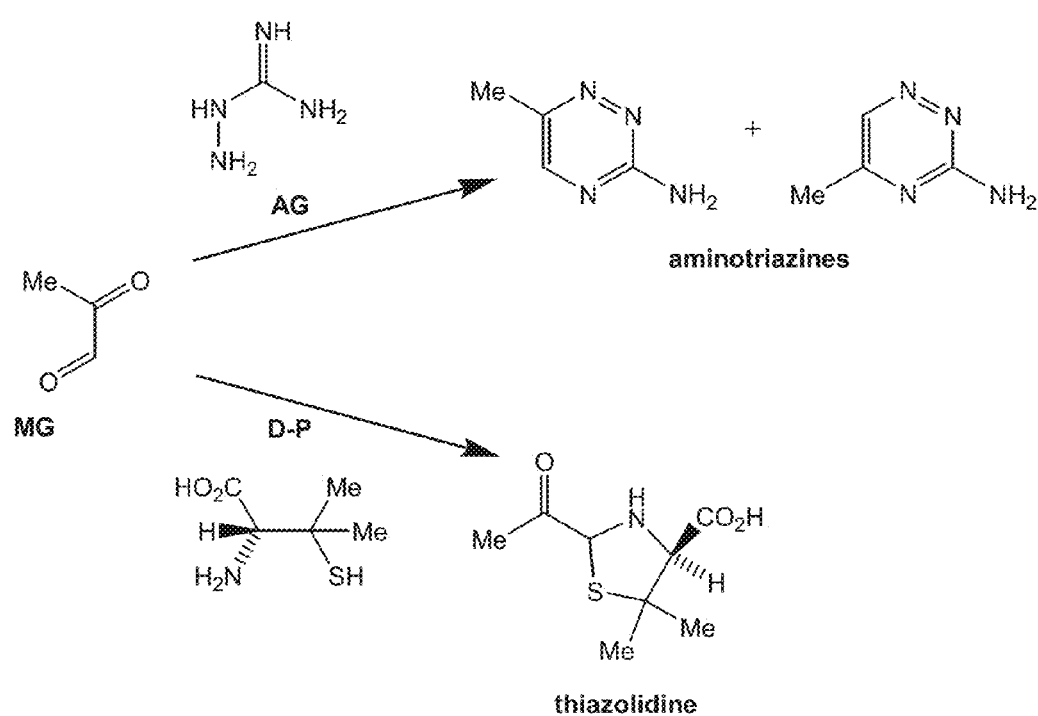
FIG. 7. Reactions of carbonyl scavengers AG and D-P with MG yield isomeric aminotriazines (top) and 2-acylthiazolidine (bottom).

One important confounding factor in the quantitation of adducts resulting from oxidative or oxoaldehyde DNA modification is artifactual product formation during sample isolation and workup. The problems surrounding the measurement of 8-oxo-dG using GC-MS and/or mildly oxidizing workup conditions have been detailed previously.[36-38] In the case of CEdG adducts, the presence of MG during the workup could complicate the accurate determination of endogenous levels. The effects of carbonyl scavenger addition prior to the enzymatic digestions were examined due to the high background levels of CEdG detected in reagent grade calf thymus DNA. Scavengers such as AG and D-P react rapidly with MG and other oxoaldehydes to yield aminotriazines and thiazolidines respectively (FIG. 7) which are relatively unreactive electrophiles. D-penicillamine reacts with MG 60 times faster than AG, and thus may be more advantageous for CEdG determinations requiring DNA isolation from complex tissue matrices.

MG bound reversibly to proteins was predominantly responsible for the formation of DNA glycation artifacts observed during the isolation and workup of dsDNA. Extraction and workup procedures which expose DNA for extended periods to cell lysates and partially purified enzyme reagents increase the probability for the ex vivo formation of CEdG, necessitating the need for carbonyl scavengers. MG-BSA conjugates prepared by incubating MG with BSA can be used as reagents to induce DNA damage in cultured mammalian cells. The data in FIG. 6 suggest that the addition of AG or D-P can largely eliminate artifactual CEdG formation. Minimizing exposure to proteins by shortening the enzymatic lysis and hydrolysis/dephosphorylation steps may also reduce the requirement for carbonyl scavengers.

A diverse array of tumor and corresponding control tissues are examined in order to determine whether the trends noted in the breast cancer specimen are a general feature of tumors which display elevated levels of glycolysis. The finding of significantly lower CEdG in breast tumors relative to adjacent normal tissue can potentially be explained by the observation that glycolytic cancers possess lower levels of MG as a result of overexpression of the glyoxalase system. This highly evolutionarily conserved system consists of two non-homologous zinc metalloenzymes Glo1 and Glo2, which act sequentially to convert MG into lactate using reduced glutathione (GSH) as a catalytic cofactor.

Glo1/2 are overexpressed around 3-5× in many breast cancers relative to normal mammary tissue, and enhanced expression of either one or both enzymes has also been observed in prostate, kidney, lung, colon, stomach, brain and ovarian cancers.[42, 43] This is a metabolic adaptation to counter the pro-apoptotic effect of MG accumulation in glycolytic tumors, which make Glo1 and Glo2 inhibitors attractive candidates for cancer therapeutics. Accordingly, another application of the present quantitative LC-MS/MS method is for monitoring the efficacy of glyoxalase inhibitors, which would induce a dose dependent increase in CEdG levels.

In sum, the new quantitative LC-MS/MS method for the measurement of CEdG improves upon (with purity and volume) and complements methods currently available for detecting protein AGEs, and allows for a more comprehensive evaluation of the role of nucleotide glycation in a wide range of human metabolic diseases, including diseases in which CEdG levels affect the disease.

The foregoing merely illustrates various embodiments. As such, the specific modifications discussed above are not to be construed as limitations on the scope of the disclosed products and methods. Equivalent embodiments are included within the contemplated scope. All references cited herein are incorporated by reference as if fully set forth herein.

REFERENCES (1) Nemet, I., Varga-Defterdarovic, L. and Turk, Z. (2006) Methylglyoxal in food and living organisms. *Mol. Nutr. Food Res.* 50, 1105-1117.

(2) Phillips, S. A. and Thornalley, P. J. (1993) The formation of methylglyoxal from triose phosphates. Investigation using a specific assay for methylglyoxal. *Eur J Biochem* 212, 101-105.

(3) Casazza, J. P., Felver, M. E. and Veech, R. L. (1984) The metabolism of acetone in rat. *J Biol Chem* 259, 231-236.

(4) Chaplen, F. W., Fahl, W. E. and Cameron, D. C. (1996) Detection of methylglyoxal as a degradation product of DNA and nucleic acid components treated with strong acid. *Anal Biochem* 236, 262-269.

(5) Murata-Kamiya, N., Kamiya, H., Kaji, H. and Kasai, H. (2000) Methylglyoxal induces G:C to C:G and G:C to T:A transversions in the supF gene on a shuttle vector plasmid replicated in mammalian cells. *Mutat Res* 468, 173-182.

(6) Lo, T. W., Selwood, T. and Thornalley, P. J. (1994) The reaction of methylglyoxal with aminoguanidine under physiological conditions and prevention of methylglyoxal binding to plasma proteins. *Biochem. Pharmacol.* 48, 1865-1870.

(7) Ahmed, N., and Thornalley, P. J. (2003) Quantitative screening of protein biomarkers of early glycation, advanced glycation, oxidation and nitrosation in cellular and extracellular proteins by tandem mass spectrometry multiple reaction monitoring. *Biochem. Soc. Trans.* 31, 1417-1422.

(8) Wautier, J. L. and Schmidt, A. M. (2004) Protein glycation: a firm link to endothelial cell dysfunction. *Circ Res* 95, 233-238.

(9) Yao, D., Taguchi, T., Matsumura, T., Pestell, R., Edelstein, D., Giardino, I., Suske, G., Ahmed, N., Thornalley, P. J., Sarthy, V. P., Hammes, H. P. and Brownlee, M. (2006) Methylglyoxal modification of mSin3A links glycolysis to angiopoietin-2 transcription. *Cell* 124, 275-286.

(10) Rahbar, S., Blumenfeld, O. and Ranney, H. M. (1969) Studies of an unusual hemoglobin in patients with diabetes mellitus. *Biochem Biophys Res Commun* 36, 838-843.

(11) Norberg, M., Eriksson, J. W., Lindahl, B., Andersson, C., Rolandsson, O., Stenlund, H. and Weinehall, L. (2006) A combination of HbA1c, fasting glucose and BMI is effective in screening for individuals at risk of future type 2 diabetes: OGTT is not needed. *J Intern Med* 260, 263-271.

(12) Edelman, D., Olsen, M. K., Dudley, T. K., Harris, A. C. and Oddone, E. Z. (2004) Utility of hemoglobin A1c in predicting diabetes risk. *J Gen Intern Med* 19, 1175-1180.

(13) Rosenstock, J., Sugimoto, D., Strange, P., Stewart, J. A., Soltes-Rak, E. and Dailey, G. (2006) Triple therapy in type 2 diabetes: insulin glargine or rosiglitazone added to combination therapy of sulfonylurea plus metformin in insulin-naive patients. *Diabetes Care* 29, 554-559.

(14) van Heijst, J. W., Niessen, H. W., Hoekman, K. and Schalkwijk, C. G. (2005) Advanced glycation end products in human cancer tissues: detection of Nepsilon-(carboxymethyl)lysine and argpyrimidine. *Ann N Y Acad Sci* 1043, 725-733.

(15) Frischmann, M., Bidmon, C., Angerer, J. and Pischetsrieder, M. (2005) Identification of DNA adducts of methylglyoxal. *Chem. Res. in Toxicol.* 18, 1586-1592.

(16) Papoulis, A., al-Abed, Y. and Bucala, R. (1995) Identification of N2-(1-carboxyethyl)guanine (CEG) as a guanine advanced glycosylation end product. *Biochemistry* 34, 648-655.

(17) Ochs, S. and Severin, T. (1994) Reaction of 2'-Deoxyguanosine with Glyceraldehyde. *Liebigs Ann Chem*, 851-853.

(18) Rahbar, S. (2007) Novel inhibitors of glycation and AGE formation. *Cell biochemistry and biophysics* 48, 147-157.

(19) Besaratinia, A., Bates, S. E., Synold, T. W., and Pfeifer, G. P. (2004) Similar mutagenicity of photoactivated porphyrins and ultraviolet A radiation in mouse embryonic fibroblasts: involvement of oxidative DNA lesions in mutagenesis. *Biochemistry* 43, 15557-15566.

(20) Phillips, S. A., Mirrlees, D. and Thornalley, P. J. (1993) Modification of the glyoxalase system in streptozotocin-induced diabetic rats. Effect of the aldose reductase inhibitor Statil. *Biochem Pharmacol* 46, 805-811.

(21) Figarola, J. L., Scott, S., Loera, S., Xi, B., Synold, T. and Rahbar, S. (2005) Renoprotective and lipid-lowering effects of LR compounds, novel advanced glycation end product inhibitors, in streptozotocin-induced diabetic rats. *Ann N Y Acad Sci* 1043, 767-776.

(22) Figarola, J. L., Scott, S., Loera, S., Tessler, C., Chu, P., Weiss, L., Hardy, J. and Rahbar, S. (2003) LR-90 a new advanced glycation endproduct inhibitor prevents progression of diabetic nephropathy in streptozotocin-diabetic rats. *Diabetologia* 46, 1140-1152.

(23) Lo, T. W., Westwood, M. E., McLellan, A. C., Selwood, T., and Thornalley, P. J. (1994) Binding and modification of proteins by methylglyoxal under physiological conditions. A kinetic and mechanistic study with N alpha-acetylarginine, N alpha-acetylcysteine, and N alpha-acetyllysine, and bovine serum albumin. *J. Biol. Chem.* 269, 32299-32305.

(24) Wondrak, G. T., Cervantes-Laurean, D., Roberts, M. J., Qasem, J. G., Kim, M., Jacobson, E. L. and Jacobson, M. K. (2002) Identification of alpha-dicarbonyl scavengers for cellular protection against carbonyl stress. *Biochem Pharmacol* 63, 361-373.

(25) Thornalley, P. J., Yurek-George, A. and Argirov, O. K. (2000) Kinetics and mechanism of the reaction of aminoguanidine with the alpha-oxoaldehydes glyoxal, methylglyoxal, and 3-deoxyglucosone under physiological conditions. *Biochem Pharmacol* 60, 55-65.

(26) Avril, N., Menzel, M., Dose, J., Schelling, M., Weber, W., Janicke, F., Nathrath, W. and Schwaiger, M. (2001) Glucose metabolism of breast cancer assessed by 18F-FDG PET: histologic and immunohistochemical tissue analysis. *J Nucl Med* 42, 9-16.

(27) Bos, R., van Der Hoeven, J. J., van Der Wall, E., van Der Groep, P., van Diest, P. J., Comans, E. F., Joshi, U., Semenza, G. L., Hoekstra, O. S., Lammertsma, A. A. and Molthoff, C. F. (2002) Biologic correlates of (18) fluorodeoxyglucose uptake in human breast cancer measured by positron emission tomography. *J Clin Oncol* 20, 379-387.

(28) Vaca, C. E., Nilsson, J. A., Fang, J. L. and Grafstrom, R. C. (1998) Formation of DNA adducts in human buccal epithelial cells exposed to acetaldehyde and methylglyoxal in vitro. *Chemico-Biological Interactions* 108, 197-208.

(29) Godschalk, R. W., Maas, L. M., Kleinjans, J. C. and Van Schooten, F. J. (1998) Influences of DNA isolation and RNA contamination on carcinogen-DNA adduct analysis by 32P-postlabeling. *Environ. Mol. Mutagen.* 32, 344-350.

(30) Schneider, M., Georgescu, A., Bidmon, C., Tutsch, M., Fleischmann, E. H., Popov, D. and Pischetsrieder, M. (2006) Detection of DNA-bound advanced glycation end-products by immunoaffinity chromatography coupled to HPLC-diode array detection. *Mo. Nutr. Food Res.* 50, 424-429.

(31) Li, H., Nakamura, S., Miyazaki, S., Morita, T., Suzuki, M., Pischetsrieder, M. and Niwa, T. (2006) N2-carboxyethyl-2'-deoxyguanosine, a DNA glycation marker, in kidneys and aortas of diabetic and uremic patients. *Kidney Int* 69, 388-392.

(32) Singh, R. and Farmer, P. B. (2006) Liquid chromatography-electrospray ionization-mass spectrometry: the future of DNA adduct detection. *Carcinogenesis* 27, 178-196.

(33) Koc, H. and Swenberg, J. A. (2002) Applications of mass spectrometry for quantitation of DNA adducts. *J. Chromatogr.* 778, 323-343.

(34) Bidmon, C., Frischmann, M. and Pischetsrieder, M. (2007) Analysis of DNA-bound advanced glycation endproducts by LC and mass spectrometry. *J. Chromatogr.* 855, 51-58.

(35) Seidel, W. and Pischetsrieder, M. (1998) DNA-glycation leads to depurination by the loss of N2-carboxyethylguanine in vitro. *Cell. Mol. Biol. (Noisy-le-Grand, France)* 44, 1165-1170.

(36) Cadet, J., D'Ham, C., Douki, T., Pouget, J. P., Ravanat, J. L. and Sauvaigo, S. (1998) Facts and artifacts in the measurement of oxidative base damage to DNA. *Free Radical Res* 29, 541-550.

(37) Rodriguez, H., Jurado, J., Laval, J. and Dizdaroglu, M. (2000) Comparison of the levels of 8-hydroxyguanine in DNA as measured by gas chromatography mass spectrometry following hydrolysis of DNA by *Escherichia coli* Fpg protein or formic acid. *Nucleic Acids Res* 28, E75.

(38) ESCODD, (2000) Comparison of different methods of measuring 8-oxoguanine as a marker of oxidative DNA damage. ESCODD (European Standards Committee on Oxidative DNA Damage). *Free Radic Res* 32, 333-341.

(39) Schupp, N., Schinzel, R., Heidland, A. and Stopper, H. (2005) Genotoxicity of advanced glycation end products: involvement of oxidative stress and of angiotensin II type 1 receptors. *Ann N Y Acad Sci* 1043, 685-695.

(40) Creighton, D. J. and Hamilton, D. S. (2001) Brief history of glyoxalase I and what we have learned about metal ion-dependent, enzyme-catalyzed isomerizations. *Arch Biochem Biophys* 387, 1-10.

(41) Thornalley, P. J. (1998) Glutathione-dependent detoxification of alpha-oxoaldehydes by the glyoxalase system: involvement in disease mechanisms and antiproliferative

(42) Rulli, A., Carli, L., Romani, R., Baroni, T., Giovannini, E., Rosi, G. and Talesa, V. (2001) Expression of glyoxalase I and II in normal and breast cancer tissues. *Breast Cancer Res Treat* 66, 67-72.
(43) Sakamoto, H., Mashima, T., Sato, S., Hashimoto, Y., Yamori, T. and Tsuruo, T. (2001) Selective activation of apoptosis program by S-p-bromobenzylglutathione cyclopentyl diester in glyoxalase I-overexpressing human lung cancer cells. *Clin Cancer Res* 7, 2513-2518.
(44) Kavarana, M. J., Kovaleva, E. G., Creighton, D. J., Wollman, M. B. and Eiseman, J. L. (1999) Mechanism-based competitive inhibitors of glyoxalase I: intracellular delivery, in vitro antitumor activities, and stabilities in human serum and mouse serum. *J Med Chem* 42, 221-228.
(45) Cao, H., Jiang, Y. and Wang, Y. (2007) Stereospecific synthesis and characterization of oligodeoxyribonucleotides containing an N2-(1-carboxyethyl)-2'-deoxyguanosine. *JACS* 129, 12123-12130.
(46) Pischetsrieder, M., Seidel, W., Munch, G. and Schinzel, R. (1999) N(2)-(1-Carboxyethyl)deoxyguanosine, a nonenzymatic glycation adduct of DNA, induces single-strand breaks and increases mutation frequencies. *Biochem Biophys Res Commun.* 264, 544-549.
(47) Lee, A. T., Plump, A., DeSimone, C., Cerami, A. and Bucala, R. (1995) A role for DNA mutations in diabetes-associated teratogenesis in transgenic embryos. *Diabetes* 44, 20-24.
(48) Eriksson, U. J., Wentzel, P., Minhas, H. S. and Thornalley, P. J. (1998) Teratogenicity of 3-deoxyglucosone and diabetic embryopathy. *Diabetes* 47, 1960-1966.
(49) La Vecchia, C., Negri, E., Franceschi, S., D'Avanzo, B., and Boyle, P. (1994) A case-control study of diabetes mellitus and cancer risk. *Br. J. Cancer.* 70, 950-953.
(50) Cowey, S., and Hardy, R. W. (2006) The metabolic syndrome: A high-risk state for cancer? *Am. J. Pathol.* 169, 1505-1522.
(51) Ahmed, N, Thornalley, P. J., Dawczynski, J., Franke, S., Strobel, J., Stein, G., Haik, G. M. (2003) Methylglyoxal-derived hydroimidazolone advanced glycation end-products of human lens proteins. *Invest Ophthalmol Vis Sci* 44, 5287-5292.
(52) Beisswenger, P. and Ruggiero-Lopez, D. (2003) Metformin inhibition of glycation processes. Diabetes Metab 29, 6S95-103.
(53) Bierhaus, A., Humpert, P. M., Morcos, M., Wendt, T., Chavakis, T., Arnold, B., Stern, D. M. and Nawroth, P. P. (2005) Understanding RAGE, the receptor for advanced glycation end products. *J Mol Med* 83, 876-886.
(54) Fosmark, D. S., Torjesen, P. A., Kilhovd, B. K., Berg, T. J., Sandvik, L., Hanssen, K. F., Agardh, C. D. and Agardh, E. (2006) Increased serum levels of the specific advanced glycation end product methylglyoxal-derived hydroimidazolone are associated with retinopathy in patients with type 2 diabetes mellitus. Metabolism: clinical and experimental 55, 232-236.
(55) Fukunaga, M., Miyata, S., Higo, S., Hamada, Y., Ueyama, S. and Kasuga, M. (2005) Methylglyoxal induces apoptosis through oxidative stress-mediated activation of p38 mitogen-activated protein kinase in rat Schwann cells. *Ann N Y Acad Sci* 1043, 151-157.
(56) Gaby, A. R. (2005) Adverse effects of dietary fructose. Altern Med Rev 10, 294-306.
(57) Han, Y., Randell, E., Vasdev, S., Gill, V., Gadag, V., Newhook, L. A., Grant, M. and Hagerty, D. (2007) Plasma methylglyoxal and glyoxal are elevated and related to early membrane alteration in young, complication-free patients with Type 1 diabetes. *Mol Cell Biochem* 305, 123-131.
(58) Li, Y., Dutta, U., Cohenford, M. A. and Dain, J. A. (2007) Nonenzymatic glycation of guanosine 5'-triphosphate by glyceraldehyde: an in vitro study of AGE formation. Bioorganic chemistry 35, 417-429.
(59) Miyata, T., van Ypersele de Strihou, C., Imasawa, T., Yoshino, A., Ueda, Y., Ogura, H., Kominami, K., Onogi, H., Inagi, R., Nangaku, M. and Kurokawa, K. (2001) Glyoxalase I deficiency is associated with an unusual level of advanced glycation end products in a hemodialysis patient. *Kidney Int* 60, 2351-2359.
(60) Price, D. L., Rhett, P. M., Thorpe, S. R. and Baynes, J. W. (2001) Chelating activity of advanced glycation end-product inhibitors. *J Biol Chem* 276, 48967-48972.
(61) Rahbar, S. (2005) The discovery of glycated hemoglobin: a major event in the study of nonenzymatic chemistry in biological systems. *Ann N Y Acad Sci* 1043, 9-19.
(62) Rahbar, S. and Figarola, J. L. (2003) Novel inhibitors of advanced glycation endproducts. *Arch Biochem Biophys* 419, 63-79.
(63) Schneider, M., Thoss, G., Hubner-Parajsz, C., Kientsch-Engel, R., Stahl, P. and Pischetsrieder, M. (2004) Determination of glycated nucleobases in human urine by a new monoclonal antibody specific for N2-carboxyethyl-2'-deoxyguanosine. Chemical research in toxicology 17, 1385-1390.
(64) Sebekova, K., Wagner, Z., Schupp, N. and Boor, P. (2007) Genomic damage and malignancy in end-stage renal failure: do advanced glycation end products contribute? *Kidney Blood Press Res* 30, 56-66.
(65) Seidel, W. and Pischetsrieder, M. (1998) Immunochemical detection of N2-[1-(1-carboxy)ethyl]guanosine, an advanced glycation end product formed by the reaction of DNA and reducing sugars or L-ascorbic acid in vitro. *Biochimica et biophysica acta* 1425, 478-484.
(66) Shinohara, M., Thornalley, P. J., Giardino, I., Beisswenger, P., Thorpe, S. R., Onorato, J. and Brownlee, M. (1998) Overexpression of glyoxalase-I in bovine endothelial cells inhibits intracellular advanced glycation end-product formation and prevents hyperglycemia-induced increases in macromolecular endocytosis. *J Clin Invest* 101, 1142-1147.
(67) Thornalley, P. J. (2003) Protecting the genome: defense against nucleotide glycation and emerging role of glyoxalase I overexpression in multidrug resistance in cancer chemotherapy. *Biochem Soc Trans* 31, 1372-1377.
(68) Vander Jagt, D. L. and Hunsaker, L. A. (2003) Methylglyoxal metabolism and diabetic complications: roles of aldose reductase, glyoxalase-I, betaine aldehyde dehydrogenase and 2-oxoaldehyde dehydrogenase. Chemico-biological interactions 143-144, 341-351.

The invention claimed is:
1. A method of detecting diabetes in a subject comprising:
(i) quantifying a $N^2$-carboxyethyl-2'-deoxyguanosine (CEdG) level in a urine sample from the subject comprising:
(a) performing a liquid chromatography electrospray ionizing tandem mass spectrometry (LC-ESI-MS/MS) assay on the urine sample using a stable isotope dilution comprising using an internal $^{15}N_5$-carboxyethyl-2'-deoxyguanosine ($^{15}N_5$-CEdG) standard comprising stereochemically pure (R) and (S) $^{15}N_5$-

CEdG or oligonucleotides containing stereochemically pure (R) and (S) $^{15}N_5$-CEdG; and
(b) measuring the CEdG level in the urine sample;
(ii) determining the subject has diabetes when the CEdG level in the urine sample is elevated as compared to a normal physiological CEdG level;
(iii) administering a treatment for diabetes to the subject determined to have diabetes; and
(iv) after administering the treatment for diabetes, determining whether the treatment is therapeutically effective by repeating steps (i) and (ii);
wherein the treatment is therapeutically effective when the level of CEdG has been reduced or returned to the normal physiological CEdG level.

2. The method of claim 1, further comprising preventing artifactual CEdG formation by adding aminoguanidine and/or D-penicillamine to the sample prior to quantifying the CEdG level in the sample.

3. The method of claim 1, wherein quantifying the level of CEdG comprises quantifying the level of diastereomers CEdG (S) and CEdG (R).

\* \* \* \* \*

UNITED STATES PATENT AND TRADEMARK OFFICE
CERTIFICATE OF CORRECTION

PATENT NO. : 9,855,233 B2
APPLICATION NO. : 14/536299
DATED : January 2, 2018
INVENTOR(S) : Samuel Rahbar et al.

Page 1 of 1

It is certified that error appears in the above-identified patent and that said Letters Patent is hereby corrected as shown below:

In the Specification

Government Interest section, Column 1, Lines 18-23, please delete:
"The present invention was made with govermnent support under City of Hope's Cancer Center Support Grant (NIH Grant No. P30 CA33572) and the California Breast Cancer Research Program for a pre-doctoral fellowship to D. Tamae (14GB-0162). The government has certain rights in the present invention."

And insert:
--This invention was made with government support under R01 CA176611, and P30 CA033572 awarded by the National Institutes of Health. The government has certain rights in the invention.--

Signed and Sealed this
First Day of July, 2025

Coke Morgan Stewart
*Acting Director of the United States Patent and Trademark Office*